United States Patent
Gray et al.

(10) Patent No.: US 6,818,806 B1
(45) Date of Patent: Nov. 16, 2004

(54) MAIZE LLS1 PROMOTER

(75) Inventors: John Gray, Toledo, OH (US); Gurmukh S. Johal, Urbandale, IA (US)

(73) Assignee: The Curators of the University of Missouri, Columbia, MO (US)

(*) Notice: Subject to any disclaimer, the term of this patent is extended or adjusted under 35 U.S.C. 154(b) by 0 days.

(21) Appl. No.: 09/327,230

(22) Filed: Jun. 7, 1999

Related U.S. Application Data

(63) Continuation-in-part of application No. 08/810,009, filed on Mar. 4, 1997.

(51) Int. Cl.[7] .......................... A01H 5/00; C07H 21/04; C12N 15/82
(52) U.S. Cl. .................... 800/298; 435/320.1; 435/419; 536/24.1; 536/24.5; 800/301; 800/302
(58) Field of Search .............................. 435/320.1, 412, 435/419, 468; 536/24.1; 800/278, 286, 279, 298, 301, 302, 320.1

(56) References Cited

U.S. PATENT DOCUMENTS

| | | | |
|---|---|---|---|
| 5,470,359 A | 11/1995 | Huffman | |
| 5,589,611 A | 12/1996 | Briggs et al. | |

FOREIGN PATENT DOCUMENTS

| | | |
|---|---|---|
| WO | WO 95/35318 | 12/1995 |
| WO | WO 97/03183 | 1/1997 |
| WO | WO 98/04586 | 2/1998 |

OTHER PUBLICATIONS

Benfey et al. Science 250: 959–966. (Nov. 1990).*
Kim et al. Plant Molecular Biology 24(1): 105–117. (1994).*
Dangl, J., Applications of Arabidoopsis Thaliana to Outstanding Issues in Plant–Pathogen Interactions, International Review of Cytolog, (1993) vol. 144, Academic Press, Inc.
Johal et al., A Tale of Two Mimics; Transposon Mutagenesis and Characterization of Two Disease Lesion Mimic Mutations of Maize, *Maydica*, (1994) 39:69–76.
Johal et al., Disease Lesion Mimics of Maize: A Model for Cell Death in Plants, *BioEssays*, (1995) vol. 17, No. 8, pp. 685–692, ICSU Press.
Dangl et al., Death Don't Have No Mercy: Cell Death Programs in Plant–Microbe Interactions, *In Plant Cell*, (Oct. 1996), vol. 8, pp. 1793–1807, American Society of Plant Physiologists.
(EMBL Sequence Data Library, Heidelberg, Germany, XP002068011, Accession No. U77346).
EMBL Sequence Data Library, Jun. 10, 1997, Heidelberg, Germany, XP002068013, Accession No. U77347.
EMBL Sequence Data Library, Heidelberg Germany, XP002068012, Accession No. 004422).
Caliebe et al., The Chloroplastic Protein Import Machinery Contains a Rieske–Type Iron–Sulfur Cluster and a Mononuclear Iron–Binding Protein, *The EMBO Journal*, (1997) vol. 16, No. 24 pp. 7342–7350, Oxford University Press.

* cited by examiner

*Primary Examiner*—Amy J. Nelson
(74) *Attorney, Agent, or Firm*—Alston & Bird LLP

(57) ABSTRACT

The present invention is drawn to a maize lls1 promoter that can be used in DNA constructs to express polynucleotides in plants, plant cells, tissues and seeds.

20 Claims, 1 Drawing Sheet

SEQUENCE LISTING

<160> NUMBER OF SEQ ID NOS: 8

<210> SEQ ID NO 1
<211> LENGTH: 2822
<212> TYPE: DNA
<213> ORGANISM: Zea mays

<400> SEQUENCE: 1

```
gcaacgcaca cagacaggca gcgatgtctt tcgcgggtca gtaaacctca ctcacacagg        60
ctattcgtct taagttttt tgttcaacat cacatacttg tgttgctaat gtaacaaaaa       120
aaattcacac gcctcacaaa cattacaata tgattcaaaa tagacactaa ccaaaccttg       180
gaggactttg tactggctag agaacaccta ctctactgct atgctgctta cccgagacag       240
aggaaataca cacgagcaac tgttgtggac ttgttgcaaa atagcaagga aaggtattag       300
```

-continued

| | | | | | |
|---|---|---|---|---|---|
| taatagcaag | cataattgta | ggagctgcaa | gtataacaat | gatagtctgc | tctttagtac | 360 |
| cttacatgta | tgaaataaaa | aactatatag | gtaaagtgaa | caacatgcgt | tatgtaaatc | 420 |
| tagcagacta | ttggattgaa | aagaattcaa | ttacaaggac | aaagaatgac | tgacgagggc | 480 |
| agcaacacaa | taactaaatg | ttccaaaatg | gtcagatatg | aagggctcga | acgcatgcac | 540 |
| ggcatgatat | gctagttggg | gccgtttccg | tcgggcttta | aagataagga | aatctggata | 600 |
| tggactaatg | atgtctaatt | tttgttagag | cctagcgccc | tagcatgcta | actagaaggt | 660 |
| taattttgtt | tctattttt | gttgcaccga | ctgagccaac | attcttttgt | ctagtagttt | 720 |
| acattttagt | tactactctc | ttcgtctaaa | aagtactata | tctccatttt | ttaaaatgtc | 780 |
| ttgcttttg | aagagcacta | tcttttaaaa | tcttgaccaa | ctatataaaa | gtacttctga | 840 |
| tacatgatag | gtttaataaa | atatataaaa | tcttatattt | ttagtaagtc | tagtcaaact | 900 |
| taagagcttt | tgatgtcgca | catagttgtt | taaacaagg | tgtttgttca | tgttcgttct | 960 |
| aatatgtgga | tagtattccg | attcatttcg | ccagaggtgt | ggctgtggat | atttggttag | 1020 |
| agcatcttca | agaaaacccg | taaatcaact | ccaaaaacgt | tttgagcctc | ccaacagtcc | 1080 |
| ccctteccct | ccccatatta | cgcgtcaagc | attgttccca | atcgtcctct | gcgcatgctg | 1140 |
| gttcccacgt | gtattttcct | cgcgcgcagt | tctgttggag | gaggaaggcg | ggacgttggc | 1200 |
| actagcgctg | gctggagatt | atggccatcg | caatcagttt | gtggcagtca | aatgctttgt | 1260 |
| tttttttggcc | gctcatgtga | gtatcatttc | tgtgaaaact | atctaaatca | atatgaatgt | 1320 |
| atatttcttt | aagtcgtcac | gataggaaga | ctccatcgtt | ctaaaaccta | aaccatgcac | 1380 |
| acatattcat | ctttctccaa | acgcaagtct | cgtgatattt | atattctcgt | gccagctaga | 1440 |
| ttatctagaa | atttagattc | ttaaaaaaat | tctttagaaa | aaaattata | ccaaacagga | 1500 |
| ccatggttta | aactattacg | gataaatagc | atgactacct | tagtatttaa | atgatatcag | 1560 |
| ttgaaatatg | tcgacttatt | ttatagttag | tattattaga | acatgtttaa | ataattatca | 1620 |
| catttaaacc | agatctacat | ataaactatt | ttgcttgtca | actgcatcgc | aaactcactt | 1680 |
| gcctaccatc | gggatcgcgc | tcgtatacaa | gtgacacact | ttaaatgatt | taagccgcga | 1740 |
| aaattataaa | tgtaccatcc | tcatttggca | agtctaaaga | tagctttacc | atacaaatga | 1800 |
| aactaaattt | aaaattccaa | gtaataatta | gaaaaactga | tttgacagtt | ttttcagtat | 1860 |
| atatttagca | gctcgctaaa | tctgaattta | gaaagttttt | ttgaaatgag | ttgagatgct | 1920 |
| cttataatgg | ttactatagg | ttgagggacg | gaagtagtag | tagaactggt | aaacaaattc | 1980 |
| gaatttgatc | tattcaactt | tgtagctact | cagcaagatg | cgaattgcaa | acatccggcg | 2040 |
| gggtggattc | cgccacggcc | cacgggtggg | ttcgtgtcgt | tctcaccgcc | ggtcaatctc | 2100 |
| ccctccgcgc | ggcgcaattc | gtcccggtgg | ggacggctag | ctggcccaat | gccaaagctc | 2160 |
| caccgacaaa | tgccgcaaag | cgccatgcgt | ggtcgcgtac | aattgcctcc | ttccccgccc | 2220 |
| ttcctcccctt | ccctgccgtg | acgcaaccac | actgcgctca | ccatcgtgta | caatgtattc | 2280 |
| tccctagccg | aaccgtatca | gtagttctta | ggggtgggcg | ttcgggttac | ccgaaatttt | 2340 |
| cgggttgggt | aattcaagtt | ttttaaattt | cgggttttga | gaatcaatac | ccgaaattac | 2400 |
| aacggatttt | tcaatacccg | gaatttcggg | tacccggaat | ttcggttcg | ggttcgggta | 2460 |
| ttcccaaact | acccgaacta | ttgtgttggc | ttcataaaaa | cacatacacc | ctattaaatt | 2520 |
| agtataaaaa | tatagtttga | ataatgatat | acatggacat | ataaaacaca | aacaatctac | 2580 |
| aatcccaagt | tatgcacact | tacacataat | tatagatgta | caaacttaaa | ttattaaagc | 2640 |

-continued

| | |
|---|---|
| atgacatgag tacatgacac atgaaagccg ggtaattcgg gtatttcggg tacccgattg | 2700 |
| tgatacccga attacccgaa ataatttcgg gttttgcaag ttgctacccg aaattcccaa | 2760 |
| acaaaattcg ggtttcgggt atttcgggtt cgggttcggg tattccaggt ttgggtttcg | 2820 |
| gg | 2822 |

<210> SEQ ID NO 2
<211> LENGTH: 4015
<212> TYPE: DNA
<213> ORGANISM: Zea mays

<400> SEQUENCE: 2

| | |
|---|---|
| ttacgggttt tttgcccagc cctactagtt cttccctcgc gttcactccc cagcgtggga | 60 |
| aaatcccgga attttcttgt tgtccactg gttttcttgc gccaaaacca ggtttctccc | 120 |
| cgttgccgtg gcagaactct gttcttgccc agtctagaag atctgcaccg ttccaaccac | 180 |
| cgactccggc cgccaagcat atagccagcg cggcgaagaa ttcccaacgc gaaagccaaa | 240 |
| acctcttcac ttcacttcac gtcgacacgt gcggggagaa tatgcgcgcg acaatcccag | 300 |
| ccctgtcgct cctggtgacg ccgcggctcc ctcgctcgc cgtgccgctg gctggaggcc | 360 |
| gcctccgcga gggcggtcgt tctcggaccc gcctccgcgt ggcggcgccg acgtccgtac | 420 |
| caggggaagc ggcggagcag gcggagccga gcacgtcggc gcccgagtcc ggcgagaagt | 480 |
| tctcgtggag ggatcactgg tacccggtct ccctcgtcga ggacctcgac cccagccgcc | 540 |
| ccaccccgtt ccagctcctc aaccgcgacc tcgtcatctg gaaggaaccc aagtccggcg | 600 |
| agtgggtcgc gctcgacgac cgctgccccc accgccttgc cccgctctcg gtacggcgac | 660 |
| ccgcatccct cctcgcctc atccgtgtcc taccggatct cttcctcgtt tcggctaatt | 720 |
| ttggtctggg catgtgcagg agggcaggat cgatgagacg gggtgcttgc agtgctcgta | 780 |
| tcacggatgg tcattcgatg gctccggcgc ctgcaccaag atcccccagg ccatgcccga | 840 |
| gggtcctgag gcccgwgcgg tgcggtcacc gaaggcgtgc gcgatcaagt tccccacct | 900 |
| cgtctcccag gggctgctct tcgtgtggcc cgatgagaat gggtggggaga aagcggccgc | 960 |
| caccaagcct ccaatgtgcg tagagtcaga ctttggactg cggctaattg gttggattca | 1020 |
| gttttgcatt tcggtgtctg aattcgatct tatttggttt caggttgccg aaagaatttg | 1080 |
| aggacccggc cttctccacg gtgacaatcc agagggactt gttctatggt tatgatacgt | 1140 |
| tgatggagaa cgtctctgat ccgtcccata tagaatttgc tcaccacaag gtacttggta | 1200 |
| cagtgagaaa gcttagttgc ttgccacact taagcaccat gatagtattt ttcagttgaa | 1260 |
| agttggtgat tcgaggaaag atgttttgtt gcaaccaatt tgtgtagttt gctaaaaaat | 1320 |
| cacctcctca atactgttta attgtgtagg cctcttatcg tttctgattg ccagtgtgca | 1380 |
| agtttaacta actgttagat cttaactgtg gatgtaccca tatatttttt ttgcatcata | 1440 |
| gttttattct ttttttactta tgctgcattg aaattcctca gaaatgactt ataatgggca | 1500 |
| aaagggctga atggctgagt ctggcctctt atcgtttcta gattgccagc gtgcaagttt | 1560 |
| aactaaggtc ccgtttggtt tgagggatta atatcagtg cctccatttt agtcccattt | 1620 |
| agtccataaa ttgacaaacg gtgggactaa acaaggact aaactgttct agtctctagt | 1680 |
| ccctcaaggg atgactctaa ggggctaaac cataaaaatc cactttttgg ccctccttca | 1740 |
| tttcagttgc actaatggcg ggaggatgtt aaggagtatt tggtcttct tatgattcat | 1800 |
| ttaatgtgtt ttgaatactt atagttttta gaaccaaaca gggagggact aaattttagt | 1860 |
| cttctaacta aactttcgtc cctggactaa aggaaccaaa ccctaactgt tagatcttaa | 1920 |

-continued

```
ctgtggatgc acccatatat attttttgcat catagttttta gttctttttt acttacgcta    1980
cttgcttagt ctgaacaggc attaataggg tgtttggttt gagggattag ttagttcacc    2040
cactcattcc tctttttcttt gtttggtttg ttgaatggag taggttggtc agtgcattat    2100
cacatcattc ctcagactag tagttagtac tagtatgaag aatgggtca ttcaaccaaa    2160
tttaaggaat tgactcatga tgcatcacca catttagaat ggagtggctc ctcaaaccaa    2220
accctataaa tgactggctg agttaattgt gctatctgtg tgtcatgaac ttgtgccggc    2280
agcatagaca aacaaaatgc tttatttttct cgggatacat ggtttcagca aatccactca    2340
tgtttcagat tttaactctt cacaggttac tggacgaaga gatagagcca ggcctttgac    2400
attcaggatg gaatcaagtg gtgcctgggg ttactcagga gcaaattctg gtaatcctcg    2460
cattactgca acttttgagg cccccttgtta tgcattaaac aagtaagttt cagaaaagta    2520
cctggtcatc tttgagtgtg gagtgattct tatttaccac ttaagcaatt cagtcgttat    2580
acggttctga acttctgtta actggcttgt acagaataga gatagacaca aagttaccca    2640
tttttggcga ccagaaatgg gtcatatgga tttgctcttt caacattcca atggccccag    2700
ggaagactcg ttctattgtc tgtagcgctc gaaactttt ccagttcaca atgccaggaa    2760
aagcatggtg gcaggtacat gtgtgtttag tgtttccttt acttaagctt tgttttccta    2820
tttgttttgt caacataatc ttttaactgc taaaacgaac ttgttctcgc gttttttgtgg    2880
gaaacaaggc aaaggtccct agtccctact gtaggcatat attattggca gagtttatta    2940
cttggtcatg tttgaattta tatgtgtaca gtcaaatgtt gatagcttct ttctcttggt    3000
gtagcttgtt cctcgatggt atgaacattg gacttcaaat ttggtctatg atggcgatat    3060
gatcgttctt caaggccagg agaagatttt cctagctgca accaaggagt cttctacgga    3120
tattaatcag cagtacacaa agatcacatt cacgcccaca caagctgatc gatttgtttt    3180
agcatgccgc acgtggctaa ggaaatttgg caatagccag ccggagtggt ttggaaatcc    3240
tacacaagaa gcattgcctt ccaccgtcct ttcaaagcgc gaggtaaaag ccatctgggt    3300
caccaaaaaa gtttcagtat aatatttgct tcagacataa aatatctgaa tatgacaacc    3360
ttttttggtgg tcaaagatct gttttgctta cattcttaat actcgatgca ttggtaagtt    3420
attacagtta tccttttttac tcgatttttc ccttctgag cagaactatt atcacgtctt    3480
cattgtttgt acacttggtt tctatgacac acaaattttt attttacatt atcagttgtc    3540
atatgaacta atgtatttac agcaacctgc ttaagtgctt agtatcacaa agggacaaat    3600
tcaatgaaat atttggaaag atagtagcgt cgaaccactc tcacagctag gcatttgaga    3660
atagttactt aactgacagc gaagttcacc ttctaccgac tggatctgga aacagtatct    3720
tgaagtagtt cacacgtaaa ccttcatcag ctgtgtttct ggcttccagt aactcatgta    3780
ttcttatgat tgactttgtg ttatgcagat gctagacaga tacgagcagc tctcgttgaa    3840
atgctcgtct tgcaaaggag catataatgc tttccagaat ctgcagaagg tattcatggg    3900
agcgacagta gtttgctgtg ctgccgctgg tattcctcca gatgttcagc tcaggctatt    3960
gatcggtgcg gctgctttgg tcagtgccgc tatagcatac gcattccatg agctc          4015
```

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: PRIMER -continued

```
<400> SEQUENCE: 3
tggggaactt gatcgcgcac gccttcgg                                              28

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: PRIMER

<400> SEQUENCE: 4
tcgggcatgg cctgggggat cttgg                                                 25

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: PRIMER

<400> SEQUENCE: 5
ggccacgcgt cgactagtac                                                       20

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: PRIMER

<400> SEQUENCE: 6
gtgctcggct ccgcctgctc cgccgcttcc cctgg                                      35

<210> SEQ ID NO 7
<211> LENGTH: 7
<212> TYPE: PRT
<213> ORGANISM: CONSENSUS SEQUENCE
<220> FEATURE:
<223> OTHER INFORMATION: CONSENSUS SEQUENCE FOR THE REISKE-TYPE [2Fe-2S]
      CLUSTER
<220> FEATURE:
<223> OTHER INFORMATION: Xaa at positions 2, 4 and 6 can be any amino
      acid.

<400> SEQUENCE: 7

Cys Xaa His Xaa Cys Xaa His
  1               5

<210> SEQ ID NO 8
<211> LENGTH: 7
<212> TYPE: PRT
<213> ORGANISM: CONSENSUS SEQUENCE
<220> FEATURE:
<223> OTHER INFORMATION: CONSENSUS SEQUENCE FOR MONONUCLEAR NON-HEME
      Fe-BINDING SITE
<220> FEATURE:
<223> OTHER INFORMATION: Xaa at positions 2, 4 and 6 can be any amino
      acid.

<400> SEQUENCE: 8

Glu Xaa Asp Xaa His Xaa His
  1               5
```

MAIZE LLS1 PROMOTER

CROSS REFERENCES TO RELATED APPLICATIONS

This application is a continuation-in-part of U.S. application Ser. No. 08/810,009, filed on Mar. 4, 1997, which is hereby incorporated herein in its entirety by reference.

FIELD OF THE INVENTION

The invention relates to the genetic manipulation of plants, particularly to novel genes and proteins and their uses in regulating cell death and disease resistance in plants.

BACKGROUND OF THE INVENTION

A host of cellular processes enable plants to defend themselves from disease caused by pathogenic agents. These processes apparently form an integrated set of resistance mechanisms that is activated by initial infection and then limits further spread of the invading pathogenic microorganism.

Subsequent to recognition of a potentially pathogenic microbe, plants can activate an array of biochemical responses. Generally, the plant responds by inducing several local responses in the cells immediately surrounding the infection site. The most common resistance response observed in both nonhost and race-specific interactions is termed the "hypersensitive response" (HR). In the hypersensitive response, cells contacted by the pathogen, and often neighboring cells, rapidly collapse and dry in a necrotic fleck. Other responses include the deposition of callose, the physical thickening of cell walls by lignification, and the synthesis of various antibiotic small molecules and proteins. Genetic factors in both the host and the pathogen determines the specificity of these local responses, which can be very effective in limiting the spread of infection.

Many environmental and genetic factors cause general leaf necrosis in maize and other plants. In addition, numerous recessive and dominant genes have been reported which cause discreet necrotic lesions to form. These lesion mutants mimic disease lesions caused by various pathogenic organisms of maize. For example, Les1, a temperature-sensitive conditional lethal mutant, mimics the appearance of *Helminthosporium maydis* on susceptible maize.

Many genes causing necrotic lesions have been reported. The pattern of lesion spread on leaves is a function of two factors: lesion initiation and individual lesion enlargement.

The lethal leaf spot-1 (lls1) mutation of maize is inherited in a recessive monogenic fashion and is characterized by the formation of scattered, necrotic leaf spots (lesions) that expand continuously to engulf the entire tissue. Since lls1 spots show striking resemblance to lesions incited by race 1 of *Cochliobolus* (*Helminthosporium*) *carbonum* on susceptible maize, this mutation has been grouped among the class of genetic defects in maize called "disease lesion mimics."

Lesion mimic mutations of maize have been shown to be specified by more than forty independent loci. These lesion mimic plants produce discreet disease-like symptoms in the absence of any invading pathogens. It is intriguing that more than two thirds of these mutations display a partially dominant, gain-of-function inheritance, making it the largest class of dominant mutants in maize, and suggesting the involvement of a signaling pathway in the induction of lesions in these mutations. Similar mutations have also been discovered in other plants including Arabidopsis and barley.

Despite the availability of the large number of lesion mimic mutations in plants, the mechanistic basis and significance of this phenomenon, and the wild-type function of the genes involved, has remained elusive. The understanding of the molecular and cellular events that are responsible for plant disease resistance remains rudimentary. This is especially true of the events controlling the earliest steps of active plant defense, recognition of a potential pathogen and transfer of the cognitive signal throughout the cell and surrounding tissue.

Diseases are particularly destructive processes resulting from specific causes and characterized by specific symptoms. Generally the symptoms can be related to a specific cause, usually a pathogenic organism. In plants, a variety of pathogenic organisms cause a wide variety of disease symptoms. Because of the lack of understanding of the plant defense system, methods are needed to protect plants against pathogen attack.

SUMMARY OF THE INVENTION

Compositions and methods for suppressing cell death and controlling disease resistance in plants are provided. The compositions, cell death suppressing proteins and the genes encoding such proteins, are useful for activating disease resistance, enhancing plant cell transformation efficiency, engineering herbicide resistance, genetically targeting cell ablations, and other methods involving the regulation of cell death and disease resistance in plants.

Additionally, novel promoter sequences are provided for the expression of genes in plants.

DETAILED DESCRIPTION OF THE INVENTION

Figure 1:
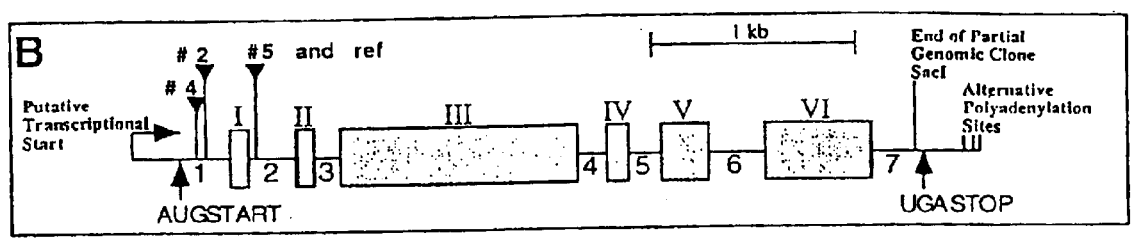
FIG. 1 sets forth the organization of the 3 kb EcoRI restriction fragment containing lls sequence, SEQ ID NO: 2.

The invention is drawn to compositions and methods for controlling cell death and disease resistance in plant cells. The compositions are proteins with putative aromatic ring-hydroxylating dioxygenase functions which act to control cell death and regulate disease resistance in plants. The proteins and genes encoding them can be used to regulate cell death and disease resistance in transformed plant cells as well as a variety of other uses. The proteins are useful in resistance to pathogens and survival of the cells particularly after pathogen attack.

One aspect of the invention is drawn to proteins which are involved in the degradation of plant phenolics, cell death-suppressing and disease resistance proteins. Such proteins are characterized by containing two consensus motifs, a Rieske-type iron-sulfur binding site, and a mononuclear iron-binding site, and putatively function as aromatic ring-hydroxylating (ARH) dioxygenases. The Rieske motif contains two cysteine and histidine residues responsible for binding an iron atom cofactor. Plant proteins containing at least one of the motifs have been identified and can be used in the methods of the present invention. Alternatively, proteins from bacteria with the Rieske motif are known in the art and can be used in the methods of the invention. Bacterial proteins of particular interest are ring-hydroxylating dioxygenases, particularly those from the cyanobacterium Synechocystis. See, for example, Gibson et al. (1984) *Microbial degradation of organic compounds*, 181–252. D. T. Gibson, ed. (New York: Marcel Dekker), pp. 181–252.

The cell death-suppressing and disease resistance proteins of the invention encompass a novel class of plant proteins.

The amino acid sequence of the lls1 protein and the corresponding gene isolated from maize are provided in parent application Ser. No. 08/810,009. However, the proteins are conserved in plants. Thus, as discussed below, methods are available for the identification and isolation of genes and proteins from any plant. Likewise, sequence similarities can be used to identify and isolate other bacterial genes and proteins. The proteins function to inhibit the spread of cell death and control disease resistance in plants. Therefore, the proteins are useful in a variety of settings involving the regulation of cell death and control of disease resistance in plants.

The Rieske motif exhibited by the proteins of the invention is shared by a class of enzymes known as ring-hydroxylating dioxygenases. The motif contains two cysteine and histidine residues responsible for binding an iron atom cofactor—residues that are shared by other proteins termed Rieske iron-sulfur proteins. The bacterial genes included in the proteins of the invention are known as catabolic operons. Thus, it is predicted that the plant proteins are related to the degradation of phenolic compound(s). In fact, a para-coumaric ester accumulates in lls1 lesioned plants, but not in normal-type siblings or wild-type siblings inoculated with the fungus Cochtiobolus heggerostrophus. While the present invention is not dependent upon any particular mechanism of action, it is believed that the cell death-suppressing function of the novel protein may be mediated by the detoxification of a phenolic compound whose cell damaging effects are fueled by light harvested by photosynthetically-functional pigments in the leaf.

Modifications of such proteins are also encompassed by the present invention. Such modifications include substitution of amino acid residues, deletions, additions, and the like. For example, the protein can be mutagenized in such a way that its activity is reduced, but not completely abolished. See, for example, Jiang et al. (1996) *J. Bacterial* 178:3133–3139, where the Tyr-221 from the mononucleate iron binding site of toluene dioxygenase was changed to Ala. This change resulted in a reduction in activity to 42% of the normal activity. A change of Tyr-266 to Ala reduced the activity to 12%. In the same manner, amino acid changes, particularly changes from Tyr to Ala, of the sequence of the proteins of the present invention can lead to increases or decreases in activity. Parent application Ser. No. 08/810,009 sets forth potential modifications, which may alter expression of the resulting protein. Such modifications can result in dominant negative inhibitors of the wild type protein. Using these sequences, the expression of lls1 can be regulated such that disease resistance can be obtained in the absence of lesions.

After each modification of the protein, the resulting protein will be tested for activity. To test for activity, plants can be transformed with the DNA sequence and tested for their response to a fungal pathogen. Of particular interest are changes that result in a reduction of activity. Such changes will confer disease resistance, yet not result in the lesion phenotype. These modified proteins, and the corresponding genes, will be useful in disease defense mechanisms in plants.

Accordingly, the proteins of the invention include naturally occurring plant and bacterial proteins and modifications thereof. Such proteins find use in preventing cell death and controlling disease resistance. The proteins are also useful in protecting plants against pathogens. In this manner, the plant is transformed with a nucleotide sequence encoding the protein. The expression of the protein in the plant prevents cell death and confers resistance to infection by plant pathogens.

The nucleotide sequences encoding the novel proteins are also provided. The lls1 gene from maize encodes the novel maize protein, which inhibits the spread of cell death from wounding or internal stresses that occur during photosynthesis. The maize gene can be utilized to isolate homologous genes from other plants, including Arabidopsis, sorghum, Brassica, wheat, tobacco, cotton, tomato, barley, sunflower, cucumber, alfalfa, soybeans, sorghum, etc.

Methods are readily available in the art for the hybridization of nucleic acid sequences. Coding sequences from other plants may be isolated according to well known techniques based on their sequence homology to the maize coding sequences set forth herein. In these techniques all or part of the known coding sequence is used as a probe which selectively hybridizes to other cell death-suppressor coding sequences present in a population of cloned genomic DNA fragments or cDNA fragments (i.e. genomic or cDNA libraries) from a chosen organism.

For example, the entire lls1 sequence or portions thereof may be used as probes capable of specifically hybridizing to corresponding coding sequences and messenger RNAs. To achieve specific hybridization under a variety of conditions, such probes include sequences that are unique among lls1 coding sequences and are preferably at least about 10 nucleotides in length, and most preferably at least about 20 nucleotides in length. Such probes may be used to amplify lls1 coding sequences from a chosen organism by the well-known process of polymerase chain reaction (PCR). This technique may be used to isolate additional lls1 coding sequences from a desired organism or as a diagnostic assay to determine the presence of lls1 coding sequences in an organism.

Such techniques include hybridization screening of plated DNA libraries (either plaques or colonies; see, e.g. Sambrook et al., *Molecular Cloning*, eds., Cold Spring Harbor Laboratory Press (1989)) and amplification by PCR using oligonucleotide primers corresponding to sequence domains conserved among the amino acid sequences (see, e.g. Innis et al., *PCR Protocols, a Guide to Methods and Applications*, eds., Academic Press (1990)).

For example, hybridization of such sequences may be carried out under conditions of reduced stringency, medium stringency or even stringent conditions (e.g., conditions represented by a wash stringency of 35–40% Formarnide with 5× Denhardt's solution, 0.5% SDS and 1×SSPE at 37° C.; conditions represented by a wash stringency of 40–45% Formarnide with 5× Denhardt's solution, 0.5% SDS, and 1×SSPE at 42° C.; and conditions represented by a wash stringency of 50% Formamide with 5× Denhardt's solution, 0.5% SDS and 1×SSPE at 42° C., respectively), to DNA encoding the cell death suppressor genes disclosed herein in a standard hybridization assay. See J. Sambrook et al., *Molecular Cloning, A Laboratory Manual 2d ed.* (1989) Cold Spring Harbor Laboratory. In general, sequences which code for a cell death suppressor and disease resistance protein and hybridize to the maize lls1 gene disclosed herein will be at least 50% homologous, 70% homologous, and even 85% homologous or more with the maize sequence. That is, the sequence similarity of sequences may range, sharing at least about 50%, about 70%, and even about 85% sequence similarity.

Generally, since leader peptides are not highly conserved between monocots and dicots, sequences can be utilized from the carboxyterminal end of the protein as probes for the isolation of corresponding sequences from any plant. Nucleotide probes can be constructed and utilized in hybridization experiments as discussed above. In this manner, even gene sequences, which are divergent in the aminoterminal region, can be identified and isolated for use in the methods of the invention.

Also provided are mutant forms of the lls1 gene (the cell death suppressor and disease resistance gene) and the proteins they encode. Methods for mutagenesis and nucleotide sequence alterations are well known in the art. See, for example, Kunkel, T. (1985) *Proc. Natl. Acad Sci. USA* 82:488492; Kunkel et al. (1987) *Methods in Enzymol.* 154:367–382; U.S. Pat. No. 4,873,192; Walker and Gaastra (eds.) *Techniques in Molecular Biology*, MacMillan Publishing Company, New York (1983) and the references cited therein. Thus, the genes and nucleotide sequences of the invention include both the naturally occurring sequences as well as mutant forms. Likewise, the proteins of the invention encompass both naturally occurring proteins as well as variations and modified forms thereof.

The nucleotide sequences encoding the proteins or polypeptides of the invention are useful in the genetic manipulation of plants. In this manner, the genes of the invention are provided in expression cassettes for expression in the plant of interest. The cassette will include 5' and 3' regulatory sequences operably linked to the gene of interest. The cassette may additionally contain at least one additional gene to be cotransformed into the organism. Alternatively, the gene(s) of interest can be provided on another expression cassette. Where appropriate, the gene(s) may be optimized for increased expression in the transformed plant. Where bacterial ring-hydroxylating dioxygenases are used in the invention, they can be synthesized using plant preferred codons for improved expression. Methods are available in the art for synthesizing plant preferred genes. See, for example, U.S. Pat. Nos. 5,380,831, 5,436,391, and Murray et al. (1989) *Nuc. Acids Res.* 17:477–498, herein incorporated by reference.

The expression cassettes may additionally contain 5' leader sequences in the expression cassette construct. Such leader sequences can act to enhance translation. Translation leaders are known in the art and include:picornavirus leaders, for example, EMCV leader (Encephalomyocarditis 5' noncoding region) (Elroy et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94; untranslated leader from the coat protein mRNA of alfalfa mosaic virus (AMV RNA 4), (Jobling et al. (1987) *Nature* 325:622–625; tobacco mosaic virus leader (TMV), (Gallie et al. (1989) *Molecular Biology of RNA*, pages 237–256; and maize chlorotic mottle virus leader (MCMV) (Lommel et al. (1991) *Virology* 81:382–385). See also, Della-Cioppa et al. (1987) *Plant Physiology* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, PCR, or the like may be employed, where insertions, deletions or substitutions, e.g. transitions and transversions, may be involved.

The compositions and methods of the present invention can be used to transform any plant. In this manner, genetically modified plants, plant cells, plant tissue, seed, and the like can be obtained. Transformation protocols may vary depending on the type of plant or plant cell, i.e. monocot or dicot, targeted for transformation. Suitable methods of transforming plant cells include microinjection (Crossway et al. (1986) *Biotechniques* 4:320–334), electroporation (Riggs et al. (1986) *Proc. Natl. Acad. Sci. USA* 83:5602–5606, Agrobacterium mediated transformation (Townsend et a. (1988) U.S. Pat. No. 5,563,055), direct gene transfer (Paszkowski et al. (1984) *EMBO J.* 3:2717–2722), and ballistic particle acceleration (see, for example, Sanford et al, U.S. Pat. No. 4,945,050; Tomes et al. (1995) "Direct DNA Transfer into Intact Plant Cells via Micropojectile Bombardment" in Plant Cell, Tissue, and Organ Culture: Fundamental Methods, ed. Gamborg and Phillips (Springer-Verlag, Berlin); and McCabe et al. (1988) *Biotechnology* 6:923–926). Also see, Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Singh et al. (1988) *Theor. Appl. Genet.* 96:319–324 (soybean); Datta et al. (1990) *Biotechnology*, 8:736–740 (rice); Klein et al. (1988) *Proc. Natl. Acad. Sci. USA* 85:4305–4309 (maize); Klein et al. (1988) *Biotechnology* 6:559–563 (maize); Tomes U.S. Pat. No. 5,240,855; Buising et al. U.S. Pat. Nos. 5,322,783 and 5,324,646 (maize); Klein et al. (1988) *Plant Physiol.* 91:440–444 (maize); Fromm et al. (1990) *Biotechnology* 8:833–839 (maize); Hooydaas et al. (1984) *Nature* (London) 311:763–764; Bytebier et al. (1987) *Proc. Natl. Acad Sci. USA* 84:5345–5349 (Liliaceae); De Wet et al. (1985) In *The Experimental Manipulation of Ovule Tissues*, ed. G. P. Chapman et al., pp. 197–209. Longman, N.Y. (pollen); Kaeppler et a. (1990) Plant Cell Reports 9:415–418; and Kaeppler et al. (1992) *Theor. Appl. Genet.* 84:560–566 (whisker-mediated transformation); D'Halluin et al. (1992) *Plant Cell*, 4:1495–1505 (electroporation); Li et al. (1993) *Plant Cell Reports* 12:250–255 and Christou et al. (1995) *Annals of Botany* 75:407413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al (1986) *Plant Cell Reports*, 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

As noted earlier, the nucleotide sequences of the invention can be utilized to protect plants from disease, particularly those caused by plant pathogens. Pathogens of the invention include, but are not limited to, viruses or viroids, bacteria, insects, fungi, and the like. Viruses include tobacco or cucumber mosaic virus, ringspot virus, necrosis virus, maize dwarf mosaic virus, etc. Specific fungal pathogens for the major crops include: Soybeans: *Phytophthora megasperma* fsp. glycinea, *Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Scierotium rolfsii,*

*Cercospora kikuchii, Cercospora sojina, Peronospora manshurica, Colletotrichum dematium (Colletotichum truncatum), Corynespora cassiicola, Septoria glycines, Phyllosticta sojicola, Alternaria alternata, Pseudomonas syringae* p.v. *glycinea, Xanthomonas campestris* p.v. *phaseoli, Microsphaera difiusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani;* Canola: *Albugo candida, Alternaria brassicae, Leptosphaeria maculans, Rhizoctonia solani, Sclerotinia scierotiorum, Mycosphaerella brassiccola, Pythium ultimum, Peronospora parasitica, Fusarium roseum, Alternaria alternata;* Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Rhizoctonia solani, Uromyces striatus, Colletotrichum trifolii* race 1 and race 2, *Leptosphaerulina briosiana, Stemphylium botryosum, Stagonospora meliloti, Scierotinia trifoliorum,* Alfalfa Mosaic Virus, *Verticillium albo-atrum, Xanthomonas campestris* p.v. *alfalfae, Aphanomyces euteiches, Stemphylium herbarum, Stemphylium alfalfae;* Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporelia herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia scierotiorum,* Aster Yellows, *Septoria helianthi, Phomopsis helianthi, Alternaria helianthi, Alternaria zinniae, Botrytis cinerea, Phoma macdonaldii, Macrophominaphaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis;* Corn: *Fusarium moniliforme* var. *subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillusflavus, Bipolaris maydis* O, T *(Cochliobolus heterostrophus), Helminthosporium carbonum* I, II & III *(Cochliobolus carbonum), Exserohilum turcicum* I, II & III, *Helminthosporium pedicellatum, Physoderma maydis, Phyllosticta maydis, Kabatiella zeae, Colletotrichum graminicola, Cercospora zeae-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvulariapallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia corotovora,* Cornstunt spiroplasma, *Diplodia macrospora, Sclerophthora macrospora, Peronosclerospora sorghi, Peronoscierospora philippinensis, Peronosclerospora maydis, Peronosclerospora sacchari, Spacelotheca reiliana, Physopella zeae, Cephalosporium maydis, Caphalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae* p.v. *syringae, Xanthomonas campestris* p.v. *holcicola, Pseudomonas andropogonis, Pucciniapurpurea, Macrophomina phaseolina, Perconia circinata, Fusarium moniliforme, Alternaria alternate, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi,* Sugarcane mosaic H, Maize Dwarf Mosaic Virus A & B, *Claviceps sorghi, Rhizoctonia solani, Acremonium strictum, Scierophthona macrospora, Peronosclerospora sorghi, Peronoscierospora philippinensis, Scierospora graminicola, Fusarium graminearum, Fusarium oxysporum, Pythium arrhenomanes, Pythium graminicola,* etc.

The nucleotide sequences also find use in enhancing transformation efficiency by suppressing cell death in bombarded cells. Thus, the sequences find particular use in transformation methods in which programmed cell death occurs. The physical wounding of particle bombardment triggers programmed cell death. The expression of the cell death-suppressor gene in a bombarded cell serves to inhibit such cell death thereby improving transformation efficiency. By "improving efficiency" is intended that the number of transformed plants recovered by a transformation event is increased. Generally, the number of transformed plants recovered is increased at least two-fold, preferably at least five-fold, more preferably at least ten-fold.

For use in improving transformation efficiency, a cell death suppressor gene is included in an expression cassette. Typically, the gene will be used in combination with a marker gene. Other genes of interest may additionally be included. The respective genes may be contained in a single expression cassette, or alternatively in separate cassettes. Methods for construction of the cassettes and transformation methods have been described above.

As noted, the cell death suppressor gene can be used in combination with a marker gene. Selectable marker genes and reporter genes are known in the art. See generally, G. T. Yarranton (1992) *Curr. Opin. Biotech.* 3:506–511; Christopherson et al. (1992) *Proc. Natl. Acad Sci. USA* 89:6314–6318; Yao et al. (1992) *Cell* 71:63–72; W. S. Reznikoff (1992) *Mol Microbiol.* 6:2419–2422; Barkley et al. (1980) *The Operon,* pp. 177–220; Hu et al. (1987) *Cell* 48:555–566; Brown et al (1987) *Cell* 49:603–612; Figge et al. (1988) *Cell* 52:713–722; and Deuschle et al. (1989) *Proc. Natl. Acad. Aci. USA* 86:5400–5404.

Plant tissue cultures and recombinant plant cells containing the proteins and nucleotide sequences, or the purified protein, of the invention may also be used in an assay to screen chemicals whose targets have not been identified to determine if they inhibit lls1 protein. Such an assay is useful as a general screen to identify chemicals which inhibit lls1 protein activity and which are therefore herbicide candidates. Alternatively, recombinantly-produced lls1 protein may be used to elucidate the complex structure of the enzyme. Such information regarding the structure of the lls1 protein may be used, for example, in the rational design of new inhibitory herbicides. It is recognized that both plant and bacterial nucleotide sequences may be utilized. The inhibitory effect on the cell-suppressor protein may be determined in an assay by monitoring the rate of cell death or alternatively by monitoring the accumulation of the activating phenolic compound, particularly the para-coumaric ester associated with lesion mutants.

If such a chemical is found, it would be useful as a herbicide, particularly if plant or bacterial mutant genes can be isolated or constructed which are not inhibited by the chemical. As indicated above, molecular techniques are available in the art for the mutagenesis and alteration of nucleotide sequences. Those sequences of interest can be selected based on resistance to the chemical. Where resistant forms of lls1 or a corresponding gene have been identified to a chemical, the chemical is also useful as a selection agent in transformation experiments. In these instances, the mutant lls1 would be used as the selectable marker gene.

The sequences of the invention also find use to genetically target cell ablations. In this manner, dominant negative nucleotide sequences can be utilized for cell ablation by expressing such negative sequences with specific tissue promoters. For example, stamen promoters can be utilized to drive the negative alleles to achieve male sterile plants. (See, for example, EP-A-0344029 and U.S. Pat. No. 5,470,359, herein incorporated by reference). Alternatively, cell ablation can be obtained by disrupting dominant negative oligonucleotides with a transposable insertion. In this manner, very specific or general patterns of cell ablations can be created. Additionally, to provide specific cell ablation, antisense oligonucleotides for lls1 or other genes of the invention can be expressed in target cells disrupting the translation, which produces the cell death suppressor proteins.

As discussed, the genes of the invention can be manipulated to enhance disease resistance in plants. In this manner, the expression or activity of the lls1 or other cell death suppressor or disease resistance gene can be altered. Such means for alteration of the gene include co-suppression, antisense, mutagenesis, alteration of the sub-cellular localization of the protein, etc. In some instances, it may be beneficial to express the gene from an inducible promoter, particularly from a pathogen inducible promoter. Such promoters include those from pathogenesis-related proteins (PR proteins) which are induced following infection by a pathogen; e.g., PR proteins, SAR proteins, beta-1,3-glucanase, chitinase, etc. See, for example, Redolfi et al. (1983) *Neth. J Plant Pathol.* 89:245–254; Uknes et al. (1992) *The Plant Cell* 4:645–656; and Van Loon (1 985) *Plant Mol. Virol.* 4:111–116.

A promoter which is capable of driving the expression of genes in a plant cell is additionally provided. The nucleotide sequence of the lls1 promoter is provided in SEQ ID NO: 1. A genomic DNA sequence comprising the lls1 gene and promoter is provided in SEQ ID NO: 2. The promoter is inducible. Generally, the promoter is induced following wounding, pathogen infection and/or metabolic upset. The promoter can be used in DNA constructs or chimeric gene constructions to drive heterologous coding sequences. The promoter and heterologous sequence will be operably linked such that the promoter drives the expression of the heterologous sequence. Plants, plant cells, tissues, and seeds can be genetically transformed with such constructs to alter the phenotype of the transformed plant, plant cell, tissue and seed. "Operably linked" includes reference to a functional linkage between a promoter and a second sequence, wherein the promoter sequence initiates and mediates transcription of he DNA sequence corresponding to the second sequence. Generally, operably linked means that the nucleic acid sequences being linked are contiguous and, where necessary to join two protein coding regions, contiguous and in the same reading frame.

The promoter may be manipulated to express heterologous resistance mechanisms at the site of pathogen infection. In the same manner, insect resistance genes, i.e. Bacillus toxins and crystal proteins, can be expressed at the onset and sites of infestation. In some circumstances it may be desirable to use the promoter to drive expression of genes that can enhance cell death in the region of a wound or cell death event triggered by stress. Accordingly, the promoter is useful for driving any gene in a plant cell, particularly genes which are needed at the site of infection or wounding. That is, the promoter is particularly useful for driving the expression of disease or insect resistance genes. The nucleotide sequence of the promoter is provided in SEQ ID NO: 1.

It is recognized that the nucleotide sequence of the promoter may be manipulated yet still retain the functional activity. Such methods for manipulation include those discussed above. Thus, the invention encompasses those modified promoter sequences, as well as promoter elements retaining the functional activity of the promoter. Such elements and modified sequences can be assayed for activity by determining the expression of a reporter gene operably linked to the promoter element or modified promoter sequence.

A genomic DNA sequence comprising the as gene and promoter are provided in SEQ ID NO: 2. The sequence can be used to construct probes to determine the location and organization of similar sequences in other plants, particularly to analyze the location of other cell death suppressing and disease resistance sequences.

The following examples are offered by way of illustration and not by way of limitation.

EXPERIMENTAL

EXAMPLE 1

Cloning of the lls1 Locus

Materials and Methods

Plant Material

The original lls1 mutant, containing the reference allele, was obtained from the Maize Genetics Coop., University of Illinois, Urbana/Champaign. Stocks containing active Mu transposons were obtained from Dr. D. Robertson, Iowa State University. The six transposon tagged mutant alleles, lls1-1 through lls1-6, were previously designated as lls*-29215, lls*-42230, lls*-1127, lls*-1424, lls*-3744, and lls*-4911, respectively (Johal et al. (1994) *A Tale of Two Mimics; Transposon Mutagenesis and characterization of Two Disease Lesion Mimic Mutations of Maize*, Maydica 39:69–76).

DNA Extraction, RFLP Mapping and Co-segregation Analysis

DNA was isolated by a urea (Dellaporta et al. (1983) *Plant Molecular Biology Reporter* 1:19–22) or CTAB (Hulbert et al. (1991) *Molecular and General Genetics* 226:377–382) extraction protocol. DNA samples (15 to 30) from either mutant or wild-type plants were pooled and digested individually with seven restriction enzymes. Southern blot analysis was performed as described by (Gardiner et al. (1993) *Genetics* 134:917–930) except that UV crosslinking and use of dextran sulfate were omitted. Blots were hybridized systematically with specific probes from different Mu elements. Mapping probes were provided either by the Maize Mapping Project at the University of Missouri or from Pioneer Hi-Bred Int. Inc. Pre-hybridizations and hybridization of southern blots was performed at 65° C. unless otherwise specified. A 3.0 kb EcorRI Mucosegregating DNA marker was cloned from an lls1*-5/lls1-ref plant using standard cloning procedures (Ausubel et al. (1994) *Current Protocols in Molecular Biology*). The Zap Express™ vector (Stratagene) was employed and packaging, screening and in vivo excision protocols performed according to manufacturer's instructions. The primer sequences (SEQ ID NOs: 3–5) for confirmation analysis were: GSP1: 5' TGG GGA ACT TGA TCG CGC ACG CCT TCG G3', GSP2: 5' TCG GGC ATG GCC TGG GGG ATC TTG G 3', and GSP3: 5' GGC CAC GCG TCG ACT AGT AC 3' (IDT, Coralville Iowa). The thermocycling regime used for confirmation analysis was 94° C. for 5 min., then cycled 40 or 42 times for 30 sec. at 94° C., 1 min. and 30 sec. at 62° C., and 1 min. at 72° C., and finally 5 min., at 72° C. Mini-libraries of cloned amplified fragments using the TA Cloning 4S vector (anvitrogen) were created and individual colonies for clones with inserts of the appropriate size. A 5' RACE fragment was used to screen a pa405 maize seedling leaf cDNA library and 3 individual clones were recovered and converted to the phagemid form by in vivo excision from the Zap Express™ (Stratagene) vector. Primers GSP1 and GSP2 were used for 5' RACE and GSP3 was used for 3' RACE using 5' and 3' RACE Kits and recommended manufacturer's instructions (GIBCO, MD). To isolate an lls1 genomic clone, a B73 partial SauIIIA library in lambda DashII was screened using a probe from a 3' RACE product spanning the lls1 gene from GSP3 to the polyadenylation site. A single positive clone was recovered and a 7.129 kb SacI fragment was subcloned into pBSKS+ (Stratagene) to create the plasmid pJG201. RFLP mapping of the Arabidopsis lls1 homolog was performed using the Recombinant Inbred (RI) lines generated from a cross between Arabidopsis ecotypes Columbia and Landsberg erccta. 48 RI lines were scored using an EcoRV polymorphism using an lls1 homolog cDNA as probe. The map position was determined on MAPMAKER using the Kosambi mapping function (Lander et al. (1987) *Genetics* 121:174–181).

Primer Extension Analysis

For primer extension analysis of the maize lls1 gene an oligonucleotide complementary to the coding strand in the lls1 gene from 139–173 bases downstream of the predicted first in-frame ATG was synthesized by DNA Technologies, Inc. (Coralville, Iowa). The oligonucleotide (SEQ ID NO: 6) GSP17 (5' GTG CTC GGC TCC GCC TGC TCC GCC GCT TCC CCT GG 3') was end-labeled with $^{32}$P. Primer extension analysis was performed by the method described by McKnight et al. (1981) *Analysis of Transcriptional Regulatory Signals of the HSV Thymidine Kinase Gene: Identification of an Upstream Control Region, Cell* 25:385–398, except for the following modifications. 40 mg of total RNA from immature tassels of a B73 inbred plant and 0.2 pmol of labeled oligonucleotide were annealed at one of either 33° C., 37° C., 45° C., or 55° C. for 4 hours. Following the extension reaction RNA in the sample was removed by adding 2 µl of 0.5 M EDTA and 1 µl of mixed RNAases (0.5 mg/ml RNAase A and 10,000 units/ml RNase TI; Ambion) and incubating at 37° C. for 30 minutes. The primer extension products were separated on a 6% denaturing polyacrylamide sequencing gel and the size of the extension product determined by comparison with a DNA sequence ladder.

Northern Blot Analysis

Total RNA was isolated from leaves of 10 leaf-stage wild-type plants in a population segregating for the LeslO1 mutation, Johal and Briggs (1992) *Science* 258:985–987. mRNA was enriched from total RNA using a magnetic bead affinity protocol (Dynal Inc. Great Neck, N.Y.). mRNA was isolated from A632 inbred plants using the MicroQuick protocol (Pharmacia, Piscataway, N.J.). Hybridizations were performed either in modified Church and Gilberts solution at 42° C. or in the following hybridization solution at 65° C.—1% casein (Technical Grade, Sigma), 1% calf skin gelatin (225 bloom, Sigma), 0.2% SDS (Mol. Biol Grade, Fisher), 0.1% Sarkosyl (IBI), 5×SSC. Transfer to nylon membrane (Magnacharge MSI, Westboro, Mass.) was performed by standard protocols, hybridizations were carried out overnight and blots were washed as indicated in the results section.

DNA Sequencing and Analysis

DNA sequencing was performed by a cycle sequence method using a SequiTherm™ Cycle Sequencing Kit (Epicentre, Madison, Wis.) according to the manufacturer's protocol. Local sequence comparisons were performed using software including ALIGN and MEGALIGN programs of the DNASTAR software package (DNASTAR Inc. Madison, Wis.). Algorithms such as the neighborhood search algorithm BLAST (Autschul et al. (1990) *Basic Local Alignment Search Tool, J Mol. Biol.* 215:403–410) or BEAUTY (Worley et al. (1995) *An Enhanced BLAST-based Search Tool that Integrates Multiple Biological Information Resources into Sequence Similarity Search Results Genome Res.* 5:173–184) were employed. Searches of the GenBank databases were performed using the National Center for Biotechnology Information's BLAST WWW Server with links to Entrez and to the Sequence Retrieval System (SRS) provided by the Human Genome Center, Baylor College of Medicine Server at Houston Texas via Internet access.

Analysis of Light Requirement for lls1 and dd Lesion Development

To determine the spectral range of light required for lesion formation, sections of leaves were clamped between 0.125 inch Plexiglas GM filters held in place by a metal stand with a side arm clamp. The following transparent filters were used: Plexiglas GM 2423 (red), 2711 (Far red), 2424 (blue), 2092 (green), 2208 (yellow), and 2422 (Amber) or Clear, (Cope Plastics Inc. St. Louis, Mo.). Transmission spectra of filters were determined by examining small sections of filters in a spectrophotometer. Leaf sections of greenhouse or field-grown plants were covered in aluminum foil to completely remove incident light. Following complete lesioning of a leaf, filters were removed to observe if lesioning had occurred in the covered region.

The lls1 Mutation is Cell Autonomous and lls1 Lesions Exhibit Altered Phenolic Metabolism and Callous Formation The expression of the lls1 phenotype is developmentally programmed: a number of round to elliptical lesions often with concentric rings of dead and dying tissue, begin as small chlorotic flecks near the tip of the first leaf at the three to four leaf stage. While these lesions continue to enlarge and eventually coalesce, new lesions initiate down the leafblade along an age gradient and cover the whole leaf within three to four days. Meanwhile, lesions have already started near the tip of the second leaf. This pattern continues and the plant dies shortly after pollen shed. Although the entire leaf tissue becomes necrotic on lls1 plants, lesions rarely develop on stalks. The lls1 mutation is cell autonomous (i.e., the effect of the gene is confined to the cell in which it is expressed) as exhibited by both revertant sectors (Johal el al. (1994) *Maydica* 69–76) and forward sectors in that the mutant phenotype does not progress into surrounding wild-type tissue. Lls1 lesions were examined for callous deposition which is frequently associated with response to pathogen infection, wounding or intercellular viral movement (Hammond-Kosack et al. (1996) *Resistance Gene-dependent Plant Defense Responses, Plant Cell* 8:1773–1791). Heavy callousing of all cell types within lesions was observed. At the edge of lesions where cells had not yet collapsed, individual bundle sheath cells were the first cells to exhibit callousing of the plasmodesmatal fields suggesting that the cells were responding to some factor or signal emanating from the dying or dead cells.

Mapping of the lls1 Locus

The original lls1 allele isolated by Ullstrup and Troyer (Ullstrup et al. (1967) *Phytopathology* 57:1282–1283) was used as the reference allele (lls1-ref). Using a combination of cytogenetic and genetic methods, the lls1 gene was initially mapped to the short arm of chromosome 1 (1S) (Hoisington (1984) *Maize Genetics Newsletter* 58:82–84). To map the gene at a higher resolution, a new population, in which the progeny segregated 1:1 for homozygous and heterozygous lls1 plants, was generated. A W23 inbred plant was fertilized with the lls1 pollen derived from an lls1-ref/lls1-ref plant, and the resulting progeny (two plants) were backcrossed with the lls1-ref homozygotes. DNA isolated from 16 mutant and 14 wild-type plants was used to examine the linkage with a number of RFLP markers. Three tightly linked RFLP markers were identified which flank the lls1 locus. The RFLP marker Php200603 is about 5 cm distal to lls1, whereas UMC157 is about 8 cm proximal to lls1. The linkage of lls1 with another marker, Php200689, could not be broken with these 30 DNAs. All three of these RFLP markers were invaluable in unequivocally classifying the mutant alleles for co-segregation analyses.

Cloning of the lls1 Locus by Transposon Tagging

Due to the lack of biochemical information on the lls1 mutation, a transposon tagging method was employed to clone the lls1 gene. This experimental approach allows genes to be cloned solely on the basis of phenotype (Bennetzen et al. (1987), *Proceedings of the UCLA Symposium: Plant Gene Systems and their Biology. ed*, 183–204). Both targeted and non-targeted approaches were employed as outlined by (Johal et al. (1994) *Maydica*, 69–76). For the targeted approach, lls1-ref/lls1-ref plants were used as male parents and crossed with wild-type plants (Lls1/Lls1) from lines active for Mu transposition. All F1 plants were expected to be of wild-type phenotype (Lls1/lls1-ref) unless a Mu insertion or some other mechanism had inactivated the Lls1 allele. Such an event would result in an lls1*/lls1-ref plant (lls1* refers to a mutant allele generated during transposon tagging) with a mutant phenotype. Three plants from approximately 30,000 F1 progeny exhibited the mutant phenotype and one of these died before shedding any pollen. The remaining two plants were crossed as male parents to B73 and Pr1 inbreds and these two new mutants have been designated lls1*-1 and lls1*-2 (lls*-29215 and lls*-42230, respectively, in (Johal et al. (1994) *Maydica*, 69–76).

A few of the progeny (10 plants) from the outcross of the mutant plants with both inbreds were RFLP genotyped to identify plants which had inherited the mutant allele (lls1*). Two plants containing the mutant allele were self-fertilized, and the F2 progeny so derived were found to segregate for the lls1 phenotype in a 1:3 ratio as expected for a recessive mutation. Two other mutant allele-containing plants from the outcross progeny were backcrossed with the lls1-ref/lls1ref mutants. The resultant progeny segregated 1:1 for mutant (lls1*-1 or -2111s1-ref) versus normal plants (Lls1-B73 or -Pr1/lls1-ref and were used for co-segregation analysis.

For non-targeted mutagenesis, Mu-active stocks were crossed to an inbred line and the resulting progeny was self-pollinated to generate F2 (M2) Mutator populations. With this approach, any recessive mutation generated during the F1 cross can be detected in the F2 generation. From more than 24,000 Mutator F2 families screened, four independent families were identified in which one-fourth of the plants exhibited a phenotype typical of lls1. The four mutant alleles have been designated lls1*-3, lls1*4, lls1*-5 and lls1*-6. A number of wild-type plants from each of these four families were pollinated with the lls1-ref/lls1-ref pollen to determine allelism between these new lls1-like mutants and the original lls1 mutant. The segregation of lls1 mutants in the progeny of most of these crosses confirmed allelism between lls1 and the new mutants. All of these mutants were outcrossed with B73 twice and backcrossed to the lls1ref/lls1-ref mutant to create populations suitable for co-segregation analysis as described above for the targeted mutants.

The next step was to confirm that the Mu elements (there are at least nine of them for Mutator) had caused these new insertional mutations. This step, called co-segregation analysis, involved Southern blot analysis to detect the linkage of a Mu element with the mutant allele in question (Bennetzen et al. (1993) *Specificity and Regulation of the Mutator Transposable Element System in Maize, Crit. Rev. Plant Sci.* 12:57–95). DNA was isolated from phenotypically mutant and wild-type plants from the segregating populations described above for each of the mutant alleles. Following identification of a putative co-segregating element, the analysis was extended employing multiple individual DNA samples digested with an appropriate restriction enzyme. In this manner a 3 kb EcoRI restriction fragment, hybridizing with the Mu8 specific probe was found to co-segregate with 66 DNA samples from the lls1*-5 mutation. This co-segregating fragment was cloned and sequenced revealing the organization indicated in FIG. 1. The DNA sequence of the right (267 bp) flank exhibited significant homology with an Arabidopsis EST of unknown function suggesting that an actual gene was disrupted by the Mu8 insertion. On sequencing the 1344 bp left flanking DNA no significant homology to known DNA sequences was detected and a Mu TIR DNA junction (terminal inverted repeats at each end of Mu elements) was not observed. Using a Mu TIR primer and either an M13 forward or reverse universal primer the left flanking (1344 bp) or right flanking (267 bp) DNA was amplified by PCR and used to probe mutant and wild-type DNA samples of all mutant alleles. This experiment revealed single band polymorphisms in nearly all alleles suggesting that this locus was disrupted in several other alleles.

The occurrence of insertions in the same locus for multiple alleles of the same mutation is considered proof that the correct locus has been tagged. A PCR based approach was used to identify Mu type insertions in the vicinity of the cloned region. The right flanking DNA from the lls1*-5 clone was sequenced as described above and primers designed for extension in each direction. These primers were used in combination with Mu TIR primers to detect amplification products in other mutant allele DNA samples but that were absent in their corresponding wild-type samples. Two such PCR polymorphisms were identified from the targeted allele lls1*-2 and the non-targeted allele lls1*4. These products hybridized strongly on a southern blot with the right flanking DNA from allele lls1*-5 indicating that these amplification products were amplified from the same locus. In addition, the amplification of a smaller (189 bp) gene specific fragment was observed in all the mutant and wild-type DNA samples from all alleles that hybridized with the right flanking DNA of the original lls1*-5 clone. Since all these samples were heterozygous for the lls5-ref allele this result indicated that the lls1-ref mutation had also resulted from a Mu insertion. Nested PCR using a Mu TIR primer and GSP2 was performed to isolate this fragment. All PCR products were directly sequenced using the GSP1 or GSP2 primers as sequencing primer and allowed identification of Mu-type insertions within 246 bp and 292 bp 5' of the insertion site of allele lls1*-5 in allele lls1*-2 and lls1*-4 respectively. It was determined that the lls1-ref allele had a Mu insertion at the same site of insertion as that of allele lls1*-5. Southern analysis using the left-flanking DNA of the lls1*-5 clone revealed that the insertion of a Mu element in the lls1-ref allele was not accompanied by a duplication event showing that the two alleles arose due to independent transposition events (explained below).

The occurrence of four independent Mutator insertions in the same locus in plants with the lls1 phenotype but not their corresponding wild-type siblings constitutes proof that a fragment of the lls1 locus had been isolated. It was observed that a Mu insertion event gave rise to the lls1-ref allele which was believed to arise in a non-Mu active background, suggesting that cosegregation analysis should be attempted with an allele of unknown origin before employing it in a targeted mutagenesis strategy since the occurrence of an insertion in the same region of the gene could obfuscate co-segregation analysis with a new allele.

The lls1 Locus Encodes a Novel Plant Protein

To characterize the lls1 locus fully a cDNA and genomic clone was isolated. Gene specific primers GSP1 and GSP3 were employed along with universal primers to amplify 5' and 3' fragments respectively of the lls1 transcript from a cDNA library constructed from 2 week old inbred PA405 seedlings. A 5' fragment was then used as a probe to screen the PA405 cDNA library and 3 individual clones were recovered and the longest phagemid named pJG200 was sequenced (GenBank Account No. U77345). This sequence was used to screen a maize EST database and another lls1 cDNA with an additional 180 bp at the 5' end was recovered. The combined sequence of these two cDNAs predicted a 521 amino acid continuous open reading frame. The identification of the termination codon was supported by a similarly located predicted termination codon in the sequence of an Arabidopsis lls1 homolog (below). A primer designed against 139 bp to 173 bp downstream of the predicted start codon of this sequence (GSP 17) was used for primer extension analysis and a 454 bp long primer extension product was observed thus predicting a 2119 bp total length transcript for the lls1 gene. In addition, the 3' ends of the cDNAs and the 3' ends of the three PCR-amplified 3'-ends were also sequenced and three different polyadenylation sites determined thus allowing for variation in the size of the full length transcript.

A 3' fragment of the lls1 gene was utilized to screen a partial Sau3A genomic library of the maize inbred line B73 in order to isolate a full-length lls1 gene sequence and a single positive clone (designated G18) was isolated. A 7129 bp SacI fragment was subcloned from the G18 genomic clone and the resulting plasmid named pJG201 was entirely sequenced (GenBank Account No. U77346). By comparison with the cDNA sequence pJG201 was found to contain almost the entire lls1 coding region and a 5' region likely to include the entire promoter. This promoter region includes an identifiable retrotransposon element of the Opie family of retrotransposons. This element exhibits near-identity with a known Opie element. In addition there is an 8 bp repeat (TAGTTCTT) directly before and after this element which is a typical direct duplication event that occurs on insertion of such transposable elements. The predicted genomic organization of the lls1 gene includes 7 exons and 6 introns. The SacI restriction site at bp 7129 is 45 bp upstream of the predicted stop codon and 320 bp upstream of the polyadenylation sites. Providing that there are no other introns in the 5' region of the gene the predicted transcriptional start site of the lls1 gene occurs at bp 3115 of the 7129 bp subclone. This transcriptional start site lies within the Opie retrotransposon element discussed above tnd thus it may be that sequences within the transposon element influence transcriptional regulation of the lls1 gene.

Southern hybridization suggests that the lls1 gene is single copy in the genome of maize since only one band was observed on Southern blots of the wild-type DNA samples of the lls1-ref allele cut with several restriction enzymes. That a duplicate of the lls1 gene exists has not yet been determined using lower stringency washes. Three bands were observed in lls1*-5 when the EcoRI digested mutant samples were probed with the left flank. A 10 bp direct repeat was not observed on each side of the Mu8 insertion in allele lls1*5. These results suggested that a rearrangement of DNA more complex than a simple Mu8 element insertion had occurred at this locus and the nature of this rearrangement was determined by comparison with the genomic sequence of the lls1 gene. The left flanking DNA comprises a direct repeat of the lls1 genornic sequence extending from the EcoRI site of Intron II to bp 43 of exon 4.

The predicted lls1 protein exhibits a largely hydrophilic protein with a pI of 7.5. No hydrophobic regions suggesting membrane association were observed. This fact suggests a cytosolic or plastidic subcellular location for the LLS 1 protein. The lls1 gene is Expressed in Mature Leaf Tissue The lls1 phenotype is developmentally expressed as described above. LLS1 appears to be needed in expanded leaves but not in very young leaves and thus lls1 transcripts may accumulate in older leaves if the gene is transcriptionally regulated. The expression of lls1 in fully expanded leaves of normal plants was examined using a partial cDNA probe that extends from the beginning of exon 2 to the end of the lls1 transcript. A weak signal was detected using 20 pg of total RNA and a high stringency wash. There did not appear to be a significant gradient in gene expression from three successively older leaves. When mRNA derived from pooled total RNA from these leaves was utilized a single transcript was readily detected. The size of this single transcript was estimated at 1.9+0.2 kb a figure which coincides closely with the full-length size determined by primer extension analysis (1.129 kb).

The lls1 Gene is Conserved Between Monocot and Dicot Plants

To determine if lls1 related genes are present in other species or organisms the predicted lls1 protein sequence was utilized to search public databases of sequences of both known and unknown functions. As indicated above, significant homology (70% nucleic acid identity) was observed between the right flanking DNA of lls1*-5 and an expressed sequence tag (EST) from *Arabidopsis thaliana*. (GenBank Account No. T45298). Three other Arabidopsis ESTs were identified that-overlap with this EST (GenBank Account Nos. N37395, H36617 and R30609). The four overlapping ESTs were obtained from the ABRC (Columbus, Ohio) and further sequenced. These sequences were organized into a single contig 1977 bp in length (GenBank Account No. U77347). The 3' end of this contig overlaps with the upstream region of the rpl9 gene (a nuclear encoded plastid ribosomal protein) ending only 109 bp upstream of the rpl9 transcriptional start. The Arabidopsis contig that exhibits 71.6% amino acid similarity over a 473 consensus length with the maize lis ORF from the available maize cDNA sequence. The amino terminus of the maize versus the Arabidopsis ORFs differ significantly indicating the possibility that each protein has a different leader peptide or that an alternative start codon is utilized. The maize lls1 sequence has therefore been utilized to detect a highly homologous gene from a dicot plant. This result prompted us to map the Arabidopsis contig and this was achieved using the recombinant Inbred (RI) lines developed by Clare Lister and Caroline Dean at the John Innes Center (Lister et al. (1993) *Plant Journal* 4:745–750). Following identification of a suitable polymorphism one EST (Account No. T45298) was used as a probe to score 48 RI lines. The map position was located on the lower arm of chromosome three between GL1 and m249. Importantly, the acdl mutation, whose cell death phenotype is reminiscent of the maize lls1, also maps in this region (Greenberg et al. (1993) *Arabidopsis Mutants Compromisedfor the Control of Cellular Damage During Pathogenesis and Aging, Plant J.* 4:327–341) suggesting that these two mutations in maize and Arabidopsis are homologous. As genomes from two divergent plant species have been found to have related lls1 genes, it is likely that any number of plant species will possess genes regulating cell survival in a manner similar to the maize lls1 gene. To further test this hypothesis we tested the linkage of maize lls1 and flanking markers to a sorghum mutation named drop-dead-1 (dd1) that is an EMS induced lesion-mimic mutation with spreading lesions highly reminiscent of lls1 lesions. A segregating mapping population was created by crossing a dd/dd line with Shangai Red Dd1/Dd1 and the progeny were allowed to self. Plants segregating for drop-dead were identified and DNA isolated from several mutant and wild-type progeny. A polymorphism for the lls1 locus could not be identified but a polymorphism for the probe PIO200640 which is ~33 cM distal to lls1 in maize was identified with HindIII. This polymorphism showed complete segregation with 14 mutant and 16 wild-type progeny strongly suggesting that this mutation maps to a region syntenic with lls1 and that lls1 and dd are homologous mutations and possibly orthologs.

lls1 Lesions are Induced by Wounding and in les-101/lls1 Double Mutants

In addition to intrinsic, developmental signals, external factors also affect lls1 expression. lls1 lesions normally appear randomly on developmentally competent areas of the leaf. However, lls1 lesions can also be triggered to initiate at any site (provided that the tissue is developmentally competent) by killing cells either by inducing an HR with an incompatible pathogen or by physical means (making pin prick wounds). The additive phenotype of the double mutant of lls1 with Les2 or Les*-101 (two dominant mimics that can initiate numerous lesions on maize leaves before they become developmentally competent to express lls1) further supports these results. On the double mutants, the early phenotype of the lesions is discrete and of the respective Les type and also of higher density as compared to that of lls1 lesions. However, as the tissue acquires developmental competence to be able to express the lls1 phenotype, most, if not all, Les sites transform into lls1 lesions that expand in an uncontrolled fashion to consume the whole leaf. Thus the internal metabolic upset and cell death events associated with a Les2 or Les*-101 lesion appear to act as a trigger for lls1 lesions.

Light is Required for lls1 and dd Lesion Formation

These observations fully support the hypothesis that lls1 functions to contain cell death from spreading, and it appears to be critical during late stages of plant development. Interestingly, the expression of lls1 lesions is completely dependent on light. The lls1 lesions typically form concentric rings where the rings exhibit a different browning coloration. The concentricity of these lesions correlates with the daily cycle suggesting that an environmental factor such as light might influence their development. To investigate the role of light in lls1 lesion expression, maize leaves were covered with aluminum foil at different stages of spontaneous lesion development. Lesions did not form on covered parts of the leaf. or the expansion of previously existing lesions would become stalled if they were covered. The formation of lesions induced by mechanical wounding was similarly affected.

Using plastic filters that transmit different wavelengths of light, leaves were covered in the region of a leaf immediately below where visible lesions were forming (distal to leaf tip) and uncovered when lesion had formed at the other side of the filter. Under full exterior sunlight (1600 to 1700 $\mu$mol/m2/sec) none of the filters could prevent lesion progression except the far-red filter which transmits less than 1% of incident sunlight (approximately 25% of full sunlight, filters that transmitted approximately 40 $\mu$mol/m2/sec or less provided a protective function. Although a move exacting study is required to define the exact amount of light required to permit lesion development, the results show that plants defective in lls1 cannot tolerate light energy beyond a uinimum threshold. Beyond this threshold the protective mechanism provided by LLS1 is essential for cell viability.

To address whether photosynthesis is responsible for the light-dependence of lesion expression, double mutants were generated with three photosynthetically-compromised mutants. iojap-1 is a recessive mutation that produces albino and pale green sectors on an otherwise normal green leaf (Han et al. (1992) *EMBO Journal* 11:4037–4046). NCS7 is a non-chromosomal striping mutation of the chloroplast genome (Neuffer et al. (1997) *Mutants of Maize* (New York: Cold Spring Harbor Laboratory Press)).

These double mutants have revealed that list lesions can only form in dark green tissues. This result indicates that some activity related to light harvest or photosynthesis may be important in the initiation and spread of lesions. Double mutants of lls1 with oil yellow-1 (Oyl1) provide further support to this interpretation. Oyl1– is a dominant mutation which by virtue of its inability to convert protoporphyrin IX to Mg-protoporphyrin, is completely devoid of chlorophyll b and has also reduced levels of chlorophyll a. On oyl1+ lls1/lls1 plants lesions initiate with a lower density and propagate very slowly in these plants and often lethality does not ensue. Intriguingly, the suppressible effect of Oyl on lls1 is not observed when the plants are grown in a greenhouse or growth chamber. Also we have observed that on an lls1/ij1 double mutant, where lesions do not initiate or develop in albino tissue, the 'death' signal (that probably allows lls1 lesions to propagate) can sometimes diffuse across (traverse) the albino tissue if the sector is narrow. This suppression of the lls1 lesions in non-photosynthetic tissue is in contrast with many other lesion mimics such as the dominant lesion mimic Les4 which readily forms lesions in the albino sectors of Les4/+ ij1/yj1 plants. These observations indicate that a process or a metabolite, which is partly diffusible and whose activity may be affected by factors including light, wounding, and pathogen invasion, is responsible for the initiation and spread of cell death associated with lls1 lesions.

The Predicted lls1 Protein Contains two Structural Motifs Highly Conserved in Bacterial Phenolic Dioxygenases While no definite function could be ascribed to lls1 from homology searches, analysis of the predicted amino acid sequence of the lls1 gene product has revealed two conserved motifs, a consensus sequence (SEQ ID NO: 7) (Cys-X-His-$X_{16-17}$-Cis-$X_2$-His) for coordinating the Rieske-type [2Fe-2S] cluster (Mason et al. (1992) The *Electron-Transport Proteins of Hydroxylating Bacterial Dioxygenases, Annu. Rev. Microbio.* 46:277–305) and a conserved mononuclear non-heme Fe-binding site (SEQ ID NO: 8) (Glu-$X_{3-4}$-Asp-X2-His-$X_{4-5}$-His) (Jiang et al. (1996) *Site-directed Mutagenesis of Conserved Amino Acids in the Alpha Subunit of Toluene Dioxygenase: Potential Mononuclear Nonheme Iron Coordination Sites, J Bacteriol.* 178:3133–3139), which are present in the a-subunit of all aromatic ring-hydroxylating (ARH) dioxygenases involved in the degradation of phenolic hydrocarbons. In addition, the spacing (~90 amino acids) between these motifs, which has recently been shown to be conserved in all ARH dioxygenases, ismprecisely maintained in LLS1, adding further evidence that LLS1 may encode a dioxygenase function. The ARH dioxygenases consist of 2 or 3 soluble proteins that interact to form an electron transport chain that transfers electrons from NADH via flavin and iron-sulfur (2Fe-2S) redox centers to a terminal dioxygenase. The latter, which is also a multimeric enzyme consisting of either α homomers or α and β heteromers, catalyzes the incorporation of two hydroxyl groups on the aromatic ring at the expense of dioxygen and NAD(P)H.

The consensus sequence of both the Rieske- and iron-binding motifs (SEQ ID NOs: 7–8) as well as the spacing between them are precisely conserved in a hypothetical protein (translated from an ORF) from Synechocystis sp. PCC6803, which in addition, exhibits 66% amino acid identity to LLS1 among a stretch of more than 100 amino acids. Additionally, the Rieske center-binding site has also been detected in the partial sequence of two seemingly related ESTs of unknown function, one each from rice and Arabidopsis.

The Rieske- and mononuclear iron binding motifs are also to be observed in two proteins from a higher plant and the green algae Chlamydomonas. The first is a protein named Tic55 which is associated with the inner chloroplast membrane import machinery complex in pea (Caliebe et al. (1997) *EMBO Journal* 16:7342–50). The second is chlorophyll a oxygenase which is involved in chlorophyll b formation from chlorophyll a in Chlamydomonas (Tanaka el al. (1998) *PNAS USA* 95:12719–23). Mutants of the latter can be fully green in appearance due to normal levels of the intermediate for chlorophyll b formation. Interestingly an NADH reductase is thought to be involved in the second step of chlorophyll b formation (Tanaka et al. supra). In Synechocystis the hypothetical protein that bears significant homology to lls1 (see above) is located directly upstream of an ORF that appears to encode NADH dehydrogenase also known as ubiquinone reductase. Upstream of the maize LLS1 gene, a partial gene containing a putative gene that exhibits homology to an aldo/keto reductase family of proteins has been found.

These results indicate that the existence of Rieske- and mononuclear iron binding motifs in a given protein is not necessarily indicative of that protein functioning as an aromatic ring-hydroxylating enzyme. Alternative interpretations could be that LLS1 may function as a modifying enzyme (e.g. a demethylase) or as an oxidation sensing regulatory mechanism. However the association of a ubiquinone reductase with the LLS1 homolog in Synechocystis may further support the possibility of LLS1 functioning in phenolic or quinone metabolism. It is not currently understood how quinones in the chloropast or mitochondrion are removed or prevented from damaging the cell if they are activated to free radical forms by excess light. It can be speculated that LLS1 may be part of a modification or detoxification process in such a scenario.

In addition each of these proteins acts as part of a multiprotein complex. Recently it has been found that an apoptogenic factor from animals named AIF (apotosis-inducing factor) bears homology to the ferredoxin reductase component of ring-hydroxylating enzymes such as benzene dioxygenase (Susin et al. (1998) *Nature* 397:441–6). It is apparent that AIF (like cytochrome c) has a dual role in the cell. The normal function occurs in the nucleus. In this context it is plausible that the cell death that occurs in LLS1 plants is due to the release of an LLS1 protein partner from it's normal cellular compartment (possibly the chloroplast instead of the mitochondrion). This interpretation provides a rationale for using the overexpression of LLS1 as a means of reducing cell death in plants. By enhancing the sequestration of a putative apoptogenic protein partner the overexpressed LLS1 protein may reduce the efficiency by which cells undergo cell death.

lls1 and *Cochliobolus carbonum*

Inoculation of lls1 leaves with *Cochliobolus carbonum* Race 1 causes a proliferation of lls1-type necrotic lesions in the middle to upper parts of the leaves. These lls1-type lesions superficially resemble *C. carbonum* lesions but they are sterile. That is, plating explants on carrot agar medium does not usually yield any *C. carbonum* fungal growth. Spontaneous lls1 lesions occurring without inoculation are also sterile and appear similar. Thus the lesions induced by *C. carbonum* inoculation are apparently lls1-type lesions and not susceptible *C. carbonum* lesions. This raises the question as to whether these lesions indicate that the lls1 mutant is susceptible to *C. carbonum* or not. It seems likely that the lls1 plants are resistant to *C. carbonum*, but that *C. carbonum* is able to trigger lls1 lesion formation. The *C. carbonum* could be acting as a stress that sets off the lls1 lesion development. After all, even abiotic stresses, such as needle pricking, will also induce lls1 lesion formation. Inoculation of lls1 leaves with *Cochiobolus carbonum* toxin plus or toxin minus causes few if any lesions to form in the middle to lower parts of the inoculated leaves. This observation is interpreted to mean that the lls1 mutation possesses induced resistance to *C. carbonum* in that area of the leaf. While both spontaneous lls1 lesions and *C. carbonum* lesions physically resemble each other, neither type was seen in this area of the leaf. In the middle transitional area there are some nascent smaller lls1 lesions. It appears as though only the upper acropetal areas of the leaf at this stage of development, are capable of forming spontaneous lls1 lesions or *C. carbonum* induced lesions.

In the lower-middle areas of lls1 leaves without any pathogen inoculation, a several fold elevation of PR1 and chitinase proteins was observed on western blots over that of Lls1/lls1 wildtype heterozygotes. Upon inoculation, the PR1 and chitinase expression in this area of the leaves was elevated slightly in lls1 and substantially in the Lls1/lls1 heterozygotes, such that after inoculation both lls1 and the wildtype heterozygotes have similar levels of PR1 and chitinase. Thus it appears that: 1) elevated PR gene expression is correlated with resistance to C. carbonum in the lower middle area of the leaves, and 2) the PR gene induction exists prior to the resistance.

lls1 and *Cochiobolus heterostrophus*

As was seen with *C. carbonum*, inoculation of lls1 leaves with *Cochiobolus heterostrophus* also causes a proliferation of lls1-type necrotic lesions in the middle to upper parts of the leaves. These lls1-type lesions are generally distinguishable from *C heterostrophus* necrotic lesions. These lls1-type lesions are also sterile; that is, plating explants on carrot agar medium does not usually yield any *C. heterostrophus* fungal growth. Spontaneous lls1 lesions occurring without inoculation are also sterile and appear similar. Thus the lesions induced by *C. heterostrophus* inoculation are apparently lls1-type lesions and not susceptible *C. heterostrophus* lesions. It appears that *C. heterostrophus* triggers formation of lls1 lesions. *C. heterostrophus* appears to be acting as a stress that sets off the lls1 lesion development. After all, even abiotic stresses, such as needle pricking, will also induced lls1 lesion formation.

Inoculation of lls1 leaves with *Cochtiobolus heterostrophus* causes few if any lesions to form in the middle to lower parts of the inoculated leaves. This observation was interpreted to mean that the lls1 mutation possesses induced resistance to *C. heterostrophus* in that area of the leaf. Spontaneous lls1 lesions and *C. heterostrophus lesions are usually distinguishable by appearance, yet neither type was observed in this area of the leaf. In the middle transitional area there are some nascent smaller lls*1 lesions, so it appears as though only the upper acropetal areas of the leaf are capable of forming lls1 lesions. However, the lack of *C. heterostrophus* lesions in this area of the leaf relative to their appearance in Lls1/lls1 and Lls1/Lls1 wildtype controls, indicates that lls1 possesses resistance to *C. heterostrophus* in that area of the leaf. That the lls1 heterozygotes are not resistant indicates that this resistance, like lls1 lesion formation, is a recessive Mendelian trait.

In the lower-middle areas of lls1 leaves without any *C. heterostrophus* inoculation, a several fold elevation of PR1 and chitinase proteins was observed on western blots over that of Lls1/lls1 wildtype heterozygotes. Upon inoculation with *C. heterostrophus*, the PR1 and chitinase in this area of the leaves is elevated slightly in lls1 and substantially in the Lls1/lls1 heterozygotes, such that after inoculation they have similar levels of PRI and chitinase. Thus it appears that elevated PR gene expression is correlated to resistance to *C. heterostrophus* in the lower middle area of the leaves, and that this elevated PR gene expression occurs prior to the inoculation and resistance.

lls1 and *Puccinia sorghi* (Rust)

Rust inoculation of lls1 plants does not necessarily induce lls1-type necrotic lesions. It was observed that rust will infect lls1 plants and produce sporulating lesions. This indicates that unlike *C. carbonum, C. heterostrophus*, and *Puccinia sorghi*, rust, a biotrophic pathogen, is able to infect lls1 and Lls/lls1 heterozygote control plants, The fact that *P. sorghi* will infect and form lesions indicates that *P. sorghi* can evade triggering lls1 lesions formation and that it can survive and grow on lls1. The lls1 mutation is therefore not necessarily rust resistant. Differences that may exist in rust susceptibility in the acropetal versus basipetal regions of the leaf have not been investigated.

Western blots revealed that mutant lls1 plants and Lls/lls1 wildtype heterozygote plants had similar levels of chitinase expression following rust inoculation. The expression of PR1, however, was slightly higher in the wildtype plants than in lls1 mutants following rust inoculation. These experiments seem to indicate that although rust is able to avoid triggering lls1-type lesions formation in lls1, it still manages to trigger at least chitinase expression. These results may have important ramifications for understanding how pathogens are detected by the plant host, and if detected, whether by the same or different mechanisms, how the signaling pathways determine whether PR gene expression activated.

To date no studies have isolated a protein(s) or gene(s) ubiquitously involved in the degradation of plant phenolics. Phenolics in plants are often sequestered in cell compartments until needed or synthesized only when required. Some phenolics however such as benzoic acid and salicylic acid have been proposed to play key roles in preconditioning cells to undergo cell death during the hypersensitive response as described by current models for systemic acquired resistance in dicot plants.

One candidate that may fit well in this role is salicylic acid (SA). SA, which exhibits a 10–50 fold increase during the HR and is also triggered in response to oxidative stresses associated with ozone or UV exposure (Hammond-Kosack and Jones (1996) *Resistance Gene-dependent Plant Defense Responses, Plant Cell* 8:1773–1791); Ryals et al. (1996) *Systemic Acquired Resistance, Plant Cell* 8:1809–1819), is known to cause $H_2O_2$ buildup (Chen et al. (1993) *Involvement of Reactive Oxygen Species in the Induction of Systemic Acquired Resistance by Salicyclic Acid in Plants, Science* 242:883–886) and transmute into a cell damaging free radical under oxidizing conditions (Durner and Klessig (1996) *Salicylic Acid is a Modulator of Tobacco and Mammalian Catalases, J. Biol Chem*. 271:28492–28501). These attributes of SA indicate that it may be a mediator of cell death in lls1 mutants, a hypothesis fully compatible with the demonstrated dependence on SA of cell death associated with a number of Arabidopsis lsd mutants (Dangl et al. (1996) *Death Don't Have no Mercy: Cell Death Programs in Plant-microbe Interactions, Plant Cell* 8:1793–1807; Weyman et al. (1996) *Suppression and Restoration of Lesion Formation in Arabidopsis lsd mutants*, Plant Cell 12:2013–2022). However, as noted above, the possibility nevertheless remains that a novel compound or mechanism is responsible for lls1-associated cell death.

The predicted association of LLS1 with an iron-sulfur cluster suggests that it may also participate in oxidation-reduction reactions. Proteins that use iron-sulfur clusters as prosthetic groups often function as biosensors of oxidants and iron (Roualt and Klausner (1996) *Iron-sulfur Clusters as Biosensors ofOxidants and Iron, Trends Biochem. Sci*. 21:174–177). LLS1 may also serve as a kind of rheostat such as that proposed for LSD1 in regulating cell death in plants (Jabs et al. (1996) *Initiation of Runaway Cell Death in an Arabidopsis Mutant by Extracellular Superoxide, Science* 273:1853–1856).

Working Model for lls1 Function

As noted earlier, the present invention is not dependent upon a particular mode of action. However, it is predicted that the LLS1 protein functions to inhibit the action of a cell "suicide factor" by degrading that factor. The suicide factor is a phenolic compound that is either a toxin or signal associated with photosynthetic stress or wounding or due to metabolic upset in the case of lls1/Les10 double mutants. Phenolics can cause superoxide production formation by donating an electron to dioxygen while in a semiquinone form (Appel (1993) *Phenolics in Ecological Interactions: The Importance of Oxidation, J Chem. Ecol.* 19:1521–1552). Photosynthetic organisms have evolved multiple mechanisms to dissipate excess energy and avoid the production of reactive oxygen intermediates (ROI) during photosynthesis. Free-radicals are scavenged by ascorbate, carotenoids, the xanthophyll cycle, alpha-tocopherol, glutathione, and various phenolics (Alscher et al. (1993), *Antioxidants in Higher Plants*). The oxidative state of a cell influences dramatically the ability of phenolics to promote free radical formation (Appel (1993) *Phenolics in Ecological Interactions: The Importance of Oxidation, J Chem. Ecol* 19:1521–1552). The development of lls1 lesions could result in cell death due to the inability to remove a toxic phenolic or signal that has accumulated in a cell.

Whereas a toxin may directly inhibit basic metabolic processes a signal may trigger a programmed cell death pathway that is reminiscent of the hypersensitive response. Lesions thus spread because the release of the contents of dying cells cause oxidative stress in surrounding cells and result in the autocatalytic production of the cell suicide factor. Alternatively a signal for cell death may activate cell death programs in surrounding cells unless it is removed. The developmental gradient of lls1 lesion expression may reflect the accumulation of a suicide factor in older cells. Young tissue does not form lesions when wounded and this may reflect the lack of accumulation of a suicide factor, the inability to yet synthesize that compound or the existence of a juvenile lls1 homolog. Protection of the plant tissue from light would directly reduce the concentration of the suicide factor and avoid lesion formation. The concentric circle appearance of lls1 lesions may thus result from variation in the production of the suicide factor due to diurnal light cycles. Revertant sectors would be resistant to this suicide factor and the ability of lesions to "traverse" pale green or albino sectors in lls1/lls1 io/io or lls1/lls1 NCS7 double mutants would reflect the concentration and diffusibility of the toxic phenolics across tissues less able or unable to produce the suicide factor. In normal tissues functional LLS1 limits the effect of a suicide factor released in the process of wounding or stress. Finally it is expected that if LLS1 affects phenolic metabolism that a change in phenolic profile would occur in lls1 plants. Significantly, this prediction is supported by the report that a para-coumaric ester accumulates in lls1 lesioned plants but not in normal wild-type siblings or wild-type siblings inoculated with the fungus *Cochliobolus heterostrophus* (Obanni et al. (1994) *Phenylpropanoid accumulation and Symptom Expression in the Lethal LeafSpot Mutant of Maize, Physiol. Mol. Plant Path.* 44:379–388).

lls1 May Play a Role in the Hypersensitive Response

A complex series of cellular events is envisaged to occur during the activation of defense responses in plants (Hammond-Kosact et al. (1996) *Resistance Gene-dependent Plant Defense Responses, Plant Cell* 8:1773–1791). Incompatible responses will often lead to the death of an infected cell within a few hours of infection. There is considerable evidence that this hypersensitive response (HR) is a form of programmed cell death activated by the plant cell. Lesion mimic mutations may cause an uncoupling of the regulatory steps of this process. Recent evidence has shown that control of cell death involves checkpoints that negatively and positively modulate the decision to progress to cell collapse. Evidence is provided by the observation that the lesion mimic phenotype of the lsd1 and lsd6 mutations of Arabidopsis are suppressed in the presence of the transgene nahG which degrades salicylic acid (SA). Application of 2,6 dichlorisonicotinic acid (a chemical inducer of systemic acquired resistance—SAR) restored lesion phenotype of these mutants (Dangl et al. (1996) Plant Cell 8:1793–1807). This result directly implicates SA in the signaling pathway that leads to cell death in these lesion mimics and that normally LSD1 and LSD6 would serve to negatively modulate that pathway. acd1 plants form spreading lesions in the presence of a functional lsd1 gene suggesting that ACD1 operates downstream or on a separate pathway from LSD1. Also there is evidence to indicate that SA donates an electron to catalase and in so doing becomes a free radical which interacts with membrane lipids to promote lipid peroxides which further promote membrane damage and cell collapse. Collectively these results suggest that acd1 functions downstream of lsd1 to inhibit a cell death pathway that is promoted by superoxide via SA and it may be that acd1 transcription is activated by LSD1. ACD1/LLS1 may degrade SA and thus negatively regulate a signaling pathway that could lead to runaway promotion of cell death. ACD1/LLS1 may be positively regulated by competing sensors of well being within the cell via the LSD1 protein and or other activators. Thus in an lls1 mutant what normally may constitute a minimal stress may become exaggerated through a runaway amplification loop and cell death pathways may be triggered resulting in lesion formation. This model predicts that nahG in an acd1/acd1 mutant will abolish lesion formation.

Cell Death Mechanisms in Plants Versus Animals

Lesion mimic genes are now providing insight into the kinds of genes involved in regulating cell death in plants. Three lesion mimic genes have now been cloned and do not have related counterparts in animal systems. This suggests that cell death is regulated in plants in a manner very different from models describing cell death regulation in animals although a role for ROI seems common to both systems. The recently cloned mlo locus from barley has been shown to encode a membrane protein and the lsd1 gene from Arabidopsis may encode a transcriptional activator. Both of these genes may normally serve to interpret external or internal stress signals and when mutated turn on or off other genes that cause cell death or cell survival respectively. The lls1 gene appears to be encode an enzyme involved in suppressing the spread of cell death through some aspect of phenolic metabolism. Phenolic production has long been long associated with cell death in plants but little understood at the molecular level. Studies of the cloned lls1 gene may afford unexpected insights into this important aspect of plant physiology.

Expression Profile of Lethal Leaf Spot 1 (lls1)

In leaves 2 and 4 of 16-days-olds wild-type seedlings (Mol7, B73), the strongest expression of lls1 is seen in both upper and lower epidermis and its derivatives (such as silica cells), in sklerenchyma cells on either side of vascular bundles, and in protoxylem elements. A weaker, but clearly discernible expression signal is observed in bundle sheath, mesophyll cells and midrib parenchyma. Expression is undetectable in metaxylem, phloem and companion cells.

In 7day-old darkgrown wild-type seedlings (B73), lls1 expression can be detected at low levels in a uniform distribution throughout most leaf cells. In leaves of the dominant lesion mimic mutant Les 101, and in the lls1 mutant itself, expression of lls1 is essentially the same as in wild-type.

For in situ expression analysis of lls1, a 0.7 kb NotI-PstI fragment from the middle of the cDNA was used to make labeled sense and antisense riboprobes.

Clones comprising the genomic sequence and cDNA sequence described herein were deposited on 14 Nov. 1996 with the American Type Culture Collection, Rockville, Md., and given accession numbers ATCC 97791 and ATCC 97792.

EXAMPLE 2

The Developmental and Inducible Pattern of lls1 Gene Expression in Maize.

Materials and Methods

Plant Material

The maize inbred line B73 was used for assessing the developmental and inducible nature of lls1 expression. lls1 expression was also assessed in the lls1-ref allele and several lesion mimic mutants.

RNA Isolation and Northern Analysis

Tissue for RNA isolation was frozen in liquid nitrogen immediately after harvesting, ground to a fine powder and added to premeasured denaturation and extraction solution (DEX) (2.0 M guanidine thiocyanate, 0.6 M ammonium thiocyanate, 0.2 M Sodium Acetate, 8% Glycerol, 50% Phenol (water saturated, pH 4.3±0.3)). Samples were vortexed and organic phase separation was effected by the addition of 0.2 vols of chloroform per vol. of DEX solution employed. RNA was precipitated from the aqueous phase using isopropanol, and the recovered pellet washed with 70% ethanol and resuspended in RNAase-free water. RNA samples were electrophoretically separated using a standard formaldehyde agarose gel procedure, and blotted into nitrocellulose (Nitrocellulose BA-S 83, 0.45 mm pore size) by capillary transfer. Blots were probed using a 50% formamide hybridization solution and following washing at various stringencies subjected to autoradiography (Auseubel et al. (1994) Current Protocols in Molecular Biology (New York: John Wiley and Sons). A partial lls1 cDNA clone was used as a probe to detect the maize lls1 transcript.

Wound Induction Experiments

The B73 inbred line was used to examine the induced expression of the maize lls1 gene by wounding. Leaves were wounded by sprinkling carborundum powder on the upper epidermis and then firmly rubbing the leaves between gloved thumb and forefinger. Plants that were wounded were exposed to light for 12 hours post wounding but for longer time intervals plants entered a period of darkness. At collection time samples were quick frozen in liquid nitrogen stored at −80° C. and prior to RNA extraction by the aforementioned procedure.

Pathogen Infection Experiments

A spore suspension of Tox+ or Tox− strains of *Helminthosporium carbonum* strains was prepared from plate cultures and 1 ml was used to inoculate the leaf whorl of Pr1, Pr or P8 seedlings at the three leaf stage or at the $8^{th}$, $9^{th}$ or $10^{th}$ week stage. A hypersensitive reaction or cell death due to pathogen invasion could be observed by 24 hours and samples were collected at 12 hr or 24 hr intervals for northern analysis.

Experiments to determine the developmental and inducible pattern of lls1 gene expression in maize.

(a) To determine the pattern of expression of lls1 during normal development, northern analysis was performed on mRNA samples isolated from several tissues of young and mature maize plants (inbred line B73). In sixty day old seedlings, expression of lls1 was detected at very low levels in the primary leaf, was barely detectable in leaf 2, and at the limit of detection in leaf 3. No signal was detected in the roots of young seedlings. By 13 days lls1 expression had increased in leaves 1 to three but was only marginally detectable in the leaf whorl (consisting of unfurled fifth leaf and lower part of leaf 4) and not at all in the roots. In adult B73 plants (tasseling stage) lls1 transcripts were readily detectable in expanded leaf tissue with a small gradient in expression that increased with leaf age. A low level of expression was detectable in leaf sheath (leaf 6) but not in immature tassels (not yet shedding), or in young ear or silk tissue. The normal expression pattern of lls1 appears to correlate directly with the extent of tissue greening and may reflect the extent to which the tissue acts as a photosynthetic source versus a sink.

(b) Previous studies had indicated that physical wounding of leaf tissue followed by exposure to light caused the formation of spreading lesions in lls1 plants. From this observation it was hypothesized that the protective function of lls1 may be induced at a transcriptional or post-transcriptional level in response to wounding. Using northern analysis it was found that lls1 gene expression increases to very high levels in leaf tissue that has been subjected to physical wounding. Leaves were wounded by sprinkling carborundum powder on the upper epidermis and then firmly rubbing the leaves between gloved thumb and forefinger. Leaves at a similar developmental age on individual plants were wounded in this manner, and collected leaf samples were quick-frozen at various time intervals following wounding for up to 24 hours. Total RNA was isolated from these samples and analyzed by northern blot using the lls1 cDNA (pJG200) as a probe. Expression of lls1 was below the limit of detection in unwounded leaves when 10 µg of total RNA was employed for analysis—although use of MRNA indicates that the lls1 transcript is indeed present in these tissues albeit at low levels. In wounded tissue of young leaves (leaf whorl and lower half of the subtending leaf of maize seedlings at the five leaf stage) the lls1 transcript was not detectable in total RNA samples until 4 to 6 hrs post wounding. In contrast, lls1 expression increased to very high levels in wounded mature leaves (fully expanded leaf 5of a 13 leaf plant). This increase could be detected beginning at approximately 3.5 hours post wounding and increasing to a maximal level around 8.5 hours and thereafter declined to low levels although a signal could still be detected at 24 hrs post-wounding. No increase in lls1 gene expression was observed in a separate experiment where samples were collected for 7 timepoints within a 2.5 hour period post-wounding. Thus lls1 expression is up-regulated in tissue where cell death is occurring although it cannot be distinguished by this result if expression occurs in dying cells or surrounding cells alone or both. This observation that lls1 is inducible also indicates that the in situ studies reflect only the levels of lls1 gene expression in the absence of cell death and that a different and more dynamic picture would likely emerge if wounded tissues were to be examined. However the cell autonomous nature of LLS1 function and the spreading nature of lls1 lesions suggest that LLS1 functions in cells surrounding dying cells to protect living cells from toxic metabolites or cell death signals that emanate outward from dying cells. See, Gray et al. (1997) *Cell* 89:25–31. LLS1 may function to remove or modify such intermediates or act as a sensor to effect other protective responses in the cell. In any event, the protective role of LLS1 is inducible by the production of new transcripts and presumably protein in stressed tissue. The signals regulating the lls1 promoter are not known at this time but candidate signals that are transduced include jasmonic acid, salicylic acid, auxins or phenolic compounds.

(c) To further investigate the range of factors influencing lls expression, northern analysis was performed on maize tissue infected with the fungal plant pathogen *Helminthosporium carbonum*. Seedlings (three leaf stage) was inoculated by spraying with a suspension of fungal spores and mature (8 to 10 wk) plants were inoculated in the leaf whorl. Young seedlings of the resistant inbred line Pr1 and the near isogenic susceptible line Pr both exhibited increased lls1 expression beginning at least by 16 hrs post-inoculation and increasing to high levels of expression by 35 to 48 hours and levels appear to decrease by 72 hrs. Higher levels of expression of the lls1 gene were observed by 24 hours if the resistant Pr I line was infected by a toxin minus *H. carbonum* isolate although this difference is not apparent at 48 hrs. When seedlings of the resistant inbred line P8 were inoculated with *H. carbonum* expression increased to high levels by 48 hours and declined again by 72 hrs. Slightly lower expression was seen when a toxin-strain was used for inoculation. High levels of expression were also observed in 8 to 10 wk old P8 plants in the 24 to 48 hours post-inoculation and also in a completely susceptible hm1hm2 line. In each of these plants a significant amount of lesioning and cell death was occurring due to either the hypersensitive response or death due to pathogen invasion in resistant and susceptible lines respectively. This result in combination with the observation that lls1 is induced in physically wounded cells suggests that cell death caused by either biotic or abiotic factors will trigger the signals to effect increased lis expression.

(d) The lack of a functional lls1 gene results in aberrant cell death which suggests that lls1 may function to protect dying cells. LLS1 may be required in other lesion mimic mutants where cells are dying and the lls1 gene may be induced in such lesioned tissue. Total RNA was isolated from leaves of several lesion mimic mutants that were exhibiting approximately 50% coverage by lesions and a leaf of similar age from a wild-type sibling was used as a control for normal expression. A very small increase was observed in lls1 expression in Les*-101 and Les22 mutant leaves compared to the wild-type control. Significantly higher levels of expression were observed in EC91 and Les14 mutant leaves. A strong and very strong increase in lls1 expression was observed in Les10 and Les9 mutant leaves. In EC91, Les14 and Les10 mutant plants two bands that hybridize with the lls1 cDNA probe were observed (approx. 2.1 and 2.3 kb in size) but the nature of these two transcripts is not yet known. The increased expression of lls1 in the Les10 mutant is observed more clearly using mRNA for northern analysis. Expression of the actin gene was used as a control for uninduced expression in mutant versus wild-type leaves. Better resolution of the transcripts by longer electrophoresis shows that there is clearly a second smaller transcript induced in the mutant leaf as compared to the wild type control. Another transcript was not observed in the lesioned Les*-101 leaves. Analysis of lls1 expression in the lls1-ref allele revealed that an lls1 hybridizing transcript is still produced in this mutant (this is not true of the alleles lls1-4 and lls1-5). Furthermore this transcript is induced several fold as would be expected if lls1 gene function is required in dying lesioned tissue. Thus, in addition to induction by wounding and pathogen infection lls1 gene expression can be induced in at least some lesion mimic plants. The differences in lls1 expression in different lesion mimics (e.g. between Les22 and Les9) may result from differences in the train of sub-cellular events that lead to cell death and different levels of production of the signals that govern lls1 gene induction.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated promoter comprising the sequence set forth in SEQ ID NO:1.
2. An expression cassette comprising the promoter of claim 1 operably linked to a heterologous coding sequence.
3. A vector comprising the expression cassette of claim 2.
4. A host cell comprising the vector of claim 3.
5. A plant which has been stably transformed with the expression cassette of claim 2.
6. The plant of claim 5, wherein said heterologous coding sequence encodes an insecticidal protein.
7. Transformed seed of the plant of claim 5.
8. A plant having stably incorporated in its genome an expression cassette, said expression cassette comprising a promoter having the sequence set forth in SEQ ID NO:1 operably linked to a heterologous coding sequence.
9. The plant of claim 8, wherein said coding sequence encodes a protein that confers resistance to insects or to fungal pathogens.
10. The plant of claim 8, wherein said coding sequence is in the antisense orientation.
11. The plant of claim 8, wherein said plant is a dicot.
12. The plant of claim 8, wherein said plant is a monocot.
13. The plant of claim 12, where in said monocot is maize.
14. Transformed seed of the plant of any one of claims 8 and 9.
15. A plant cell having stably incorporated in its genome an expression cassette, said expression cassette comprising a promoter having the sequence set forth in SEQ ID NO:1 operably linked to a heterologous coding sequence.
16. The plant cell of claim 15, wherein said coding sequence encodes a protein that confers resistance to insects or to fungal pathogens.
17. The plant cell of claim 15, wherein said coding sequence is in the antisense orientation.
18. The plant cell of claim 15, wherein said plant cell is from a dicotyledonous plant.
19. The plant cell of claim 15, wherein said plant cell is from a monocotyledonous plant.
20. The plant cell of claim 19, wherein said monocotyledonous plant is maize.

* * * * *

UNITED STATES PATENT AND TRADEMARK OFFICE
CERTIFICATE OF CORRECTION

PATENT NO. : 6,818,806 B1
DATED : November 16, 2004
INVENTOR(S) : Gray et al.

It is certified that error appears in the above-identified patent and that said Letters Patent is hereby corrected as shown below:

Column 38,
Line 4, "and 9" should read -- and 9-13 --.

Signed and Sealed this

Fifth Day of April, 2005

JON W. DUDAS
*Director of the United States Patent and Trademark Office*